(12) United States Patent
Ruman et al.

(10) Patent No.: US 10,478,350 B2
(45) Date of Patent: Nov. 19, 2019

(54) MALE INCONTINENCE ARTICLE HAVING AN ABSORBENT CUP

(71) Applicant: KIMBERLY-CLARK WORLDWIDE, INC., Neenah, WI (US)

(72) Inventors: Marcille F. Ruman, Oshkosh, WI (US); Sarah A. Kleuskens, Neenah, WI (US); Phillip L. Hutchison, Woodstock, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 689 days.

(21) Appl. No.: 14/868,533

(22) Filed: Sep. 29, 2015

(65) Prior Publication Data

US 2016/0089275 A1   Mar. 31, 2016

Related U.S. Application Data

(60) Provisional application No. 62/057,685, filed on Sep. 30, 2014.

(51) Int. Cl.
*A61F 13/15* (2006.01)
*A61F 13/20* (2006.01)
*A61F 13/471* (2006.01)
*A61F 13/47* (2006.01)

(52) U.S. Cl.
CPC ........ *A61F 13/471* (2013.01); *A61F 13/4704* (2013.01)

(58) Field of Classification Search
CPC ............................. A61F 13/471; A61F 13/551
See application file for complete search history.

(56) References Cited

U.S. PATENT DOCUMENTS

| 5,074,853 | A | 12/1991 | Bryant |
| 5,556,393 | A | 9/1996 | Ronnberg |
| 5,695,485 | A | 12/1997 | Duperret et al. |
| 5,702,381 | A | 12/1997 | Cottenden |
| 5,827,257 | A | 10/1998 | Fujioka et al. |
| 6,129,719 | A * | 10/2000 | Nozaki ................. A61F 13/471 604/385.01 |
| 6,336,919 | B1 | 1/2002 | Davis et al. |

(Continued)

FOREIGN PATENT DOCUMENTS

| EP | 0225909 B1 | 11/1989 |
| GB | 2436291 A | 9/2007 |

(Continued)

*Primary Examiner* — Michele M Kidwell
(74) *Attorney, Agent, or Firm* — Armstrong Teasdale LLP

(57) ABSTRACT

A male incontinence article includes a liquid permeable liner, a liquid impermeable outer cover, and an absorbent core disposed between the liner and the outer cover. The article is configurable from a laid flat configuration to a use configuration. The article has, in the use configuration, an absorbent cup and an upstanding wall that extends upward from the cup. The cup has a closed bottom, a sidewall extending upward from the closed bottom, and an open top. The closed bottom and the sidewall cooperatively define an interior chamber adapted to receive at least a portion of the user's penis. Suitable packaging and methods of manufacturing such an article are also disclosed.

22 Claims, 29 Drawing Sheets

(56) References Cited

U.S. PATENT DOCUMENTS

| | | | |
|---|---|---|---|
| 6,371,950 B1* | 4/2002 | Roslansky | A61F 13/471 |
| | | | 604/385.28 |
| 6,402,729 B1* | 6/2002 | Boberg | A61F 13/4753 |
| | | | 604/385.28 |
| 6,409,712 B1 | 6/2002 | Dutari | |
| 6,565,548 B1* | 5/2003 | Glaug | A61F 5/453 |
| | | | 604/349 |
| 7,172,584 B2 | 2/2007 | Karami | |
| 7,341,580 B2 | 3/2008 | Hamilton-Vance | |
| D614,767 S | 4/2010 | Webster | |
| 7,993,318 B2 | 8/2011 | Olsson et al. | |
| 8,740,868 B2 | 6/2014 | Chambers | |
| 2004/0111073 A1 | 6/2004 | Hermansson et al. | |
| 2006/0106356 A1 | 5/2006 | McVicker et al. | |
| 2007/0043330 A1* | 2/2007 | Lankhof | A61F 13/531 |
| | | | 604/378 |
| 2009/0182297 A1* | 7/2009 | Hedstrom | A61F 13/4915 |
| | | | 604/385.13 |
| 2010/0036343 A1* | 2/2010 | Hernandez | A61F 13/4756 |
| | | | 604/374 |
| 2013/0138070 A1 | 5/2013 | Drevik | |
| 2015/0126951 A1* | 5/2015 | Sharkey | A61F 13/471 |
| | | | 604/385.03 |

FOREIGN PATENT DOCUMENTS

| | | |
|---|---|---|
| JP | 2012200453 A | 10/2012 |
| JP | 5407374 B2 | 2/2014 |
| JP | 5446550 B2 | 3/2014 |
| WO | 9316666 A1 | 9/1993 |
| WO | 2005/044166 A1 * 5/2005 ............ A61F 13/471 |
| WO | 2010039068 A1 | 4/2010 |
| WO | 2011139192 A1 | 11/2011 |
| WO | 2013114839 A1 | 8/2013 |

\* cited by examiner

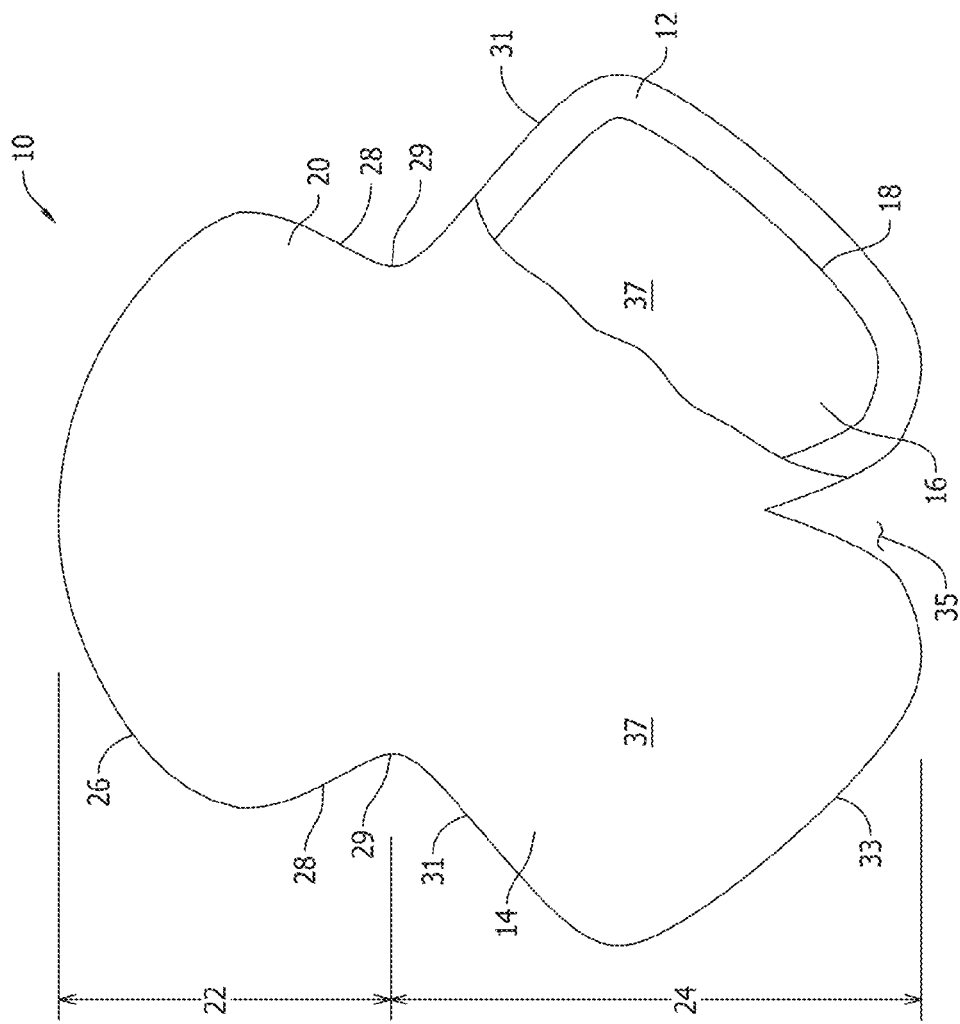
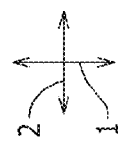
FIG. 2

MALE INCONTINENCE ARTICLE HAVING AN ABSORBENT CUP

CROSS REFERENCE TO RELATED APPLICATION

This application claims the benefit of U.S. Provisional Application No. 62/057,685 filed Sep. 30, 2014, which is incorporated herein by reference in its entirety.

FIELD

The field of this invention relates generally to incontinence articles for use by males, and more particularly to incontinence articles having an absorbent cup to take in and retain fluids discharged by the user.

BACKGROUND

Absorbent articles currently available for male incontinence include, for example, liners, pads, pants and briefs. Pant and brief type incontinence articles, which are typically disposable absorbent garments, resemble and are worn in the manner of conventional undergarments. However, incontinence garments are intended for taking in and retaining a substantial volume of fluid, such as an entire urination event. As a result, pants and brief type incontinence articles are usually bulky and typically non-discrete. Moreover, pants and brief type incontinence articles often present emotional and/or psychological obstacles to the user.

Thus, when dealing with relatively light incontinence, men usually rely on liners and pads. While there are liners and pads specifically designed for men, most of them resemble feminine care products in their fundamental structure. That is, most liners and pads for men are designed to lie flat and adhere to the user's underwear. While this approach has been successful for women, it has some limitations for men because of the variable positioning and movement of the user's penis. Moreover, such liners and pads are often associated with women and, as a result, often present emotional and psychological obstacles for a male user.

Some manufacturers of absorbent articles have attempted to make more three dimensional articles that cradle or cover the male anatomy (i.e., the penis and/or scrotum of the user). However, these articles are often uncomfortable for the user (e.g., elasticized absorbent sleeve that covers the penis, penile clip with absorbent sleeve that covers the penis). Moreover, these articles often fail to provide full leakage protection.

Accordingly, there is a need for incontinence articles specifically designed for males that are masculine and comfortable to the user (e.g., not constraining or constricting the user's penis) while providing all around protection from leaks by gently and fully surrounding at least the distal end of the penis of the user.

SUMMARY

In one aspect, a male incontinence article generally comprises a liquid permeable liner, a liquid impermeable outer cover, and an absorbent core disposed between the liner and the outer cover. The article is configurable from a laid flat configuration to a use configuration. The article has, in the use configuration, an absorbent cup and an upstanding wall that extends upward from the cup. The cup has a closed bottom, a sidewall extending upward from the closed bottom, and an open top. The closed bottom and the sidewall cooperatively define an interior chamber adapted to receive at least a portion of the user's penis. In one suitable embodiment, the interior chamber has a volume between about 50 cm$^3$ and about 600 cm$^3$. In another suitable embodiment, the interior chamber has a volume between about 100 cm$^3$ and about 300 cm$^3$.

In one embodiment, the sidewall of the cup tapers outward from the closed bottom to the open top such that the sidewall has greater width adjacent the open top as compared to the width of the sidewall adjacent the closed bottom. In one such embodiment, the sidewall of the cup is frustum.

The open top of cup is defined by an upper edge of the sidewall. In one suitable embodiment, at least a portion of the upper edge is concave and wherein the concaved portion of the upper edge is opposed to the upstanding wall.

In another aspect, a male incontinence article generally comprises a liquid permeable liner, a liquid impermeable outer cover, and an absorbent core disposed between the liner and the outer cover. The article has a use configuration and, in the use configuration, comprises an absorbent cup and an upstanding wall that extends upward from the cup. The cup has a closed bottom, a sidewall extending upward from the closed bottom, and an open top defined by an upper edge of the sidewall. The closed bottom and the sidewall cooperatively define an interior chamber adapted to receive at least a portion of the user's penis. The cup has a first height H1 at a location adjacent the upstanding wall, and a second height H2 spaced from the upstanding wall that is less than the first height.

In one suitable embodiment the first height H1 is between about 60 mm and about 120 mm and, more suitably, between about 80 mm and about 100 mm. In one suitable embodiment, the second height H2 is generally aligned with the longitudinal axis of the article and is between about 60 mm and about 120 mm and, more suitably, between about 80 mm and about 100 mm.

In yet another aspect, a male incontinence article generally comprises a liquid permeable liner, a liquid impermeable outer cover, and an absorbent core disposed between the liner and the outer cover. The article has a use configuration and, in the use configuration, comprises an absorbent cup and an upstanding wall that extends upward from the cup. The cup has a closed bottom, a sidewall extending upward from the closed bottom, and an open top defined by an upper edge of the sidewall. The closed bottom and the sidewall cooperatively define an interior chamber adapted to receive at least a portion of the user's penis. The cup has a bond seam and a covering material that covers the bond seam and thereby prevents the seam from coming into direct contact with the user's skin during use of the male incontinence article.

In one embodiment, the bond seam is aligned with the longitudinal axis of the article and extends in the longitudinal direction of the article the entire height of the sidewall. Suitably, the bond seam is one of a fin seam, a butt seam and a lap seam.

In one suitable embodiment, the covering material covers at least a portion of the upper edge of the sidewall of the cup.

In still another aspect, a package generally comprises at least one male incontinence article and underwear for use with the article. The underwear comprises an interior pocket sized and shaped for receiving the male incontinence article. The male incontinence article comprises a liquid permeable liner, a liquid impermeable outer cover, and an absorbent core disposed between the liner and the outer cover. The article is configurable from a laid flat configuration to a use configuration. The article has, in the use configuration, an absorbent cup and an upstanding wall that extends upward from the cup. The cup has a closed bottom, a sidewall extending upward from the closed bottom, and an open top. The closed bottom and the sidewall cooperatively define an interior chamber adapted to receive at least a portion of the user's penis.

In one suitable embodiment, the package is adapted to receive a plurality of male incontinence articles in a stacked configuration. In one such embodiment, the package is adapted to receive two stacks of stacked articles.

In another aspect, a method of manufacturing male incontinence articles generally comprises feeding a first web of material and placing a plurality of discrete absorbent cores on the first web such that adjacent absorbent cores are aligned in opposite orientations relative to each other. A second web of material is fed in a superimposed relationship with the absorbent cores and the first web. The first web is bonded to the second web about a periphery of the absorbent cores to define a bonded area and to capture the absorbent cores between the first and second webs. The first and second webs are cut within the bonded area to form discrete male incontinence articles.

In one suitable embodiment, the plurality of discrete absorbent cores are aligned in a cross machine direction and placed in a nested arrangement on the first web.

In yet another aspect, a method of manufacturing male incontinence articles having an upper portion and a lower portion generally comprises feeding a first web of material and placing a plurality of discrete absorbent cores on the first web. A second web of material is fed in a superimposed relationship with the absorbent cores and the first web. The first web is bonded to the second web about a periphery of the absorbent cores to define a bonded area and to capture the absorbent cores between the first and second webs. The first and second webs are cut within the bonded area to form discrete male incontinence articles. A cup is formed in each of the discrete male incontinence articles about a forming member by moving opposed side edges of the lower portion in relationship with one another and bonding the side edges together.

In one suitable embodiment, the side edges of the lower portion are moved about a cylindrical forming member having a conical tip. The side edges can be bonded together along a longitudinally extending bond seam to form one of a fin seam, a butt seam and an overlapping seam.

In still another aspect, a method of manufacturing male incontinence articles having an upper portion and a lower portion generally comprises feeding a first web of material and placing a plurality of discrete absorbent cores on the first web. A second web of material is fed in a superimposed relationship with the absorbent cores and the first web. The first web is bonded to the second web about a periphery of the absorbent cores to define a bonded area and to capture the absorbent cores between the first and second webs. The first and second webs are cut within the bonded area to form discrete male incontinence articles. A cup is formed in each of the discrete male incontinence articles about a forming member by moving opposed side edges of the lower portion in relationship with one another and bonding the side edges together to form a bonding seam. The bonding seam is covered with a covering material.

In one suitable embodiment, the side edges are bonded the entire height of the cup along a longitudinally extending bonding seam. The covering material covers at least a portion of an upper edge of the sidewall of the cup in one suitable embodiment.

In one embodiment, the method further comprises stacking a plurality of the discrete male incontinence articles such that at least some of the cups are disposed in cups of other articles, and packaging the stacked male incontinence articles in a package.

In an aspect, a male incontinence article comprises a liquid permeable liner having a peripheral edge, a liquid impermeable outer cover having a peripheral edge, and an absorbent core disposed between the liner and the outer cover. The absorbent core has a peripheral edge. A barrier extends adjacent the perimeter of the liner.

In another aspect, a male incontinence article generally comprises a liquid permeable liner having a peripheral edge, a liquid impermeable outer cover having a peripheral edge, and an absorbent core disposed between the liner and the outer cover. The absorbent core has a peripheral edge and the peripheral edges of the liner and the outer cover extending beyond the peripheral edge of the absorbent core. The liner and the outer cover are secured together along their respective peripheral edges and outboard of the peripheral edge of the absorbent core. The liner, the outer cover, and the absorbent core are ovate and cooperatively define a pocket that is sized and shaped to receive at least the distal end of the user's penis.

In yet another aspect, a package generally comprises a plurality of the male incontinence articles in a stacked configuration wherein overlying articles are nested with the respective underlying article. The package comprises a cylindrical tube having a bottom and a lid. At least one of the bottom and the lid are selectively removeable to provide access to the articles positioned in the tube.

In still yet another aspect, a male incontinence article generally comprises a liquid permeable liner having a peripheral edge, a liquid impermeable outer cover having a peripheral edge, and an absorbent core disposed between the liner and the outer cover. The absorbent core has a peripheral edge and the peripheral edges of the liner and the outer cover extend beyond the peripheral edge of the absorbent core. The liner and the outer cover are secured together along their respective peripheral edges to define a bonded area disposed outboard of the peripheral edge of the absorbent core. A barrier is positioned adjacent the perimeter of the liner and is bonded to the liner at the bonded area.

Other objects and features will be in part apparent and in part pointed out hereinafter.

BRIEF DESCRIPTION OF THE DRAWINGS

FIG. 2 is a back plan view of the male incontinence article in a laid flat configuration showing a liquid impermeable outer cover of the article, a portion of the outer cover being cut away to show underlying components.

Corresponding reference characters indicate corresponding parts throughout the drawings.

DETAILED DESCRIPTION OF THE DRAWINGS

Figure 1:
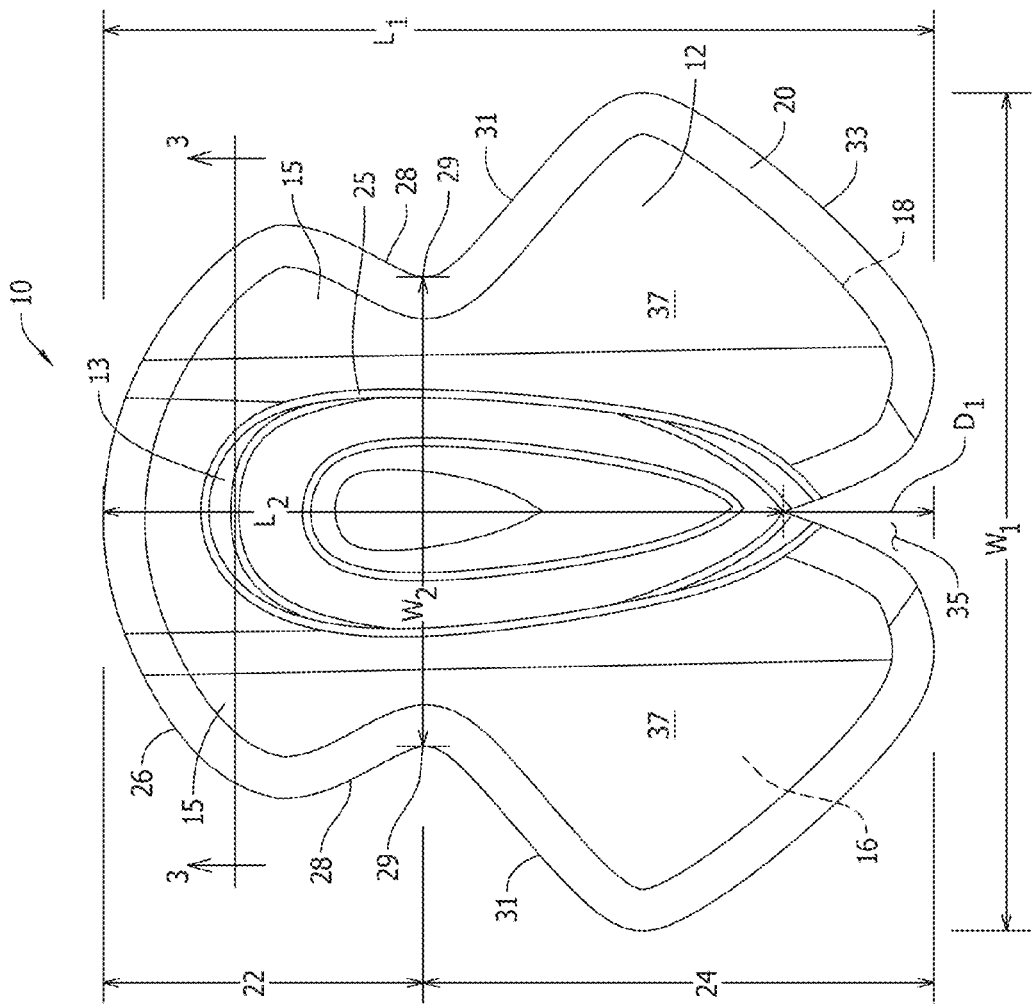
FIG. 1 is a front plan view of one suitable embodiment of a male incontinence article in a laid flat configuration showing a liquid permeable liner of the article.
Figure 3:
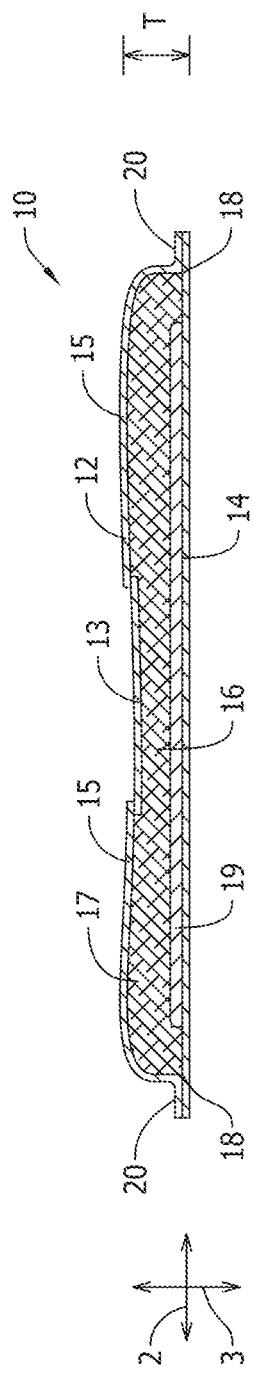
FIG. 3 is a cross section taken along line 3-3 of FIG. 1.
Figure 4:
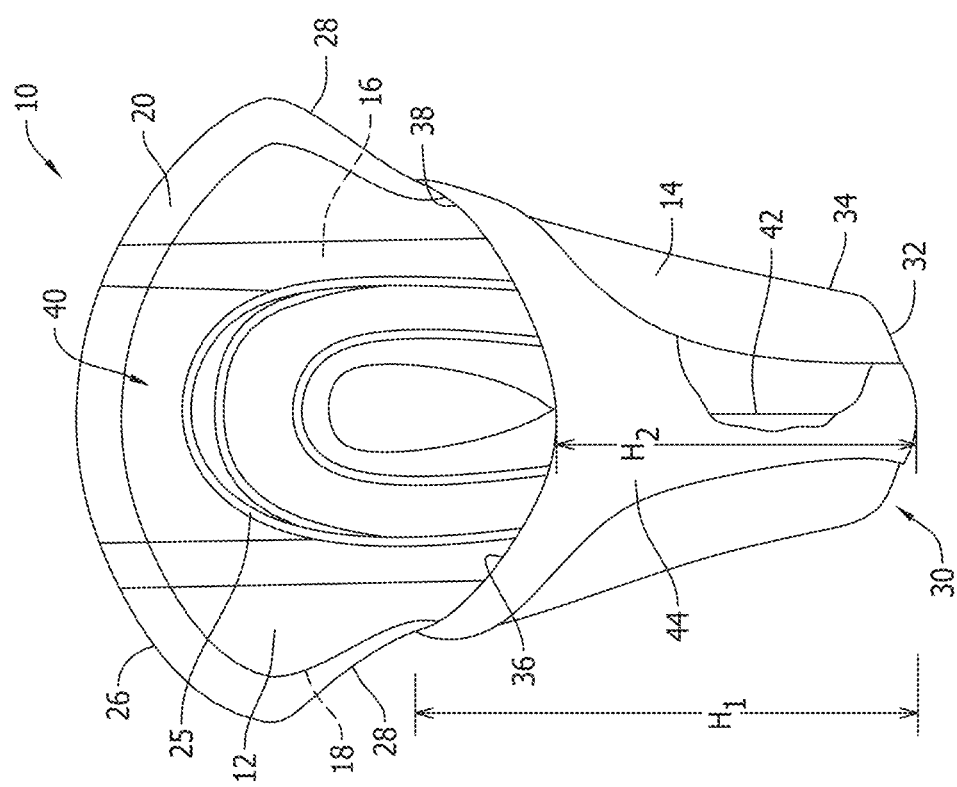
FIG. 4 is a front perspective of the male incontinence article of FIG. 1 in a use configuration wherein the article is positioned to define a cup and an upstanding wall extending from the cup.
Figure 5:
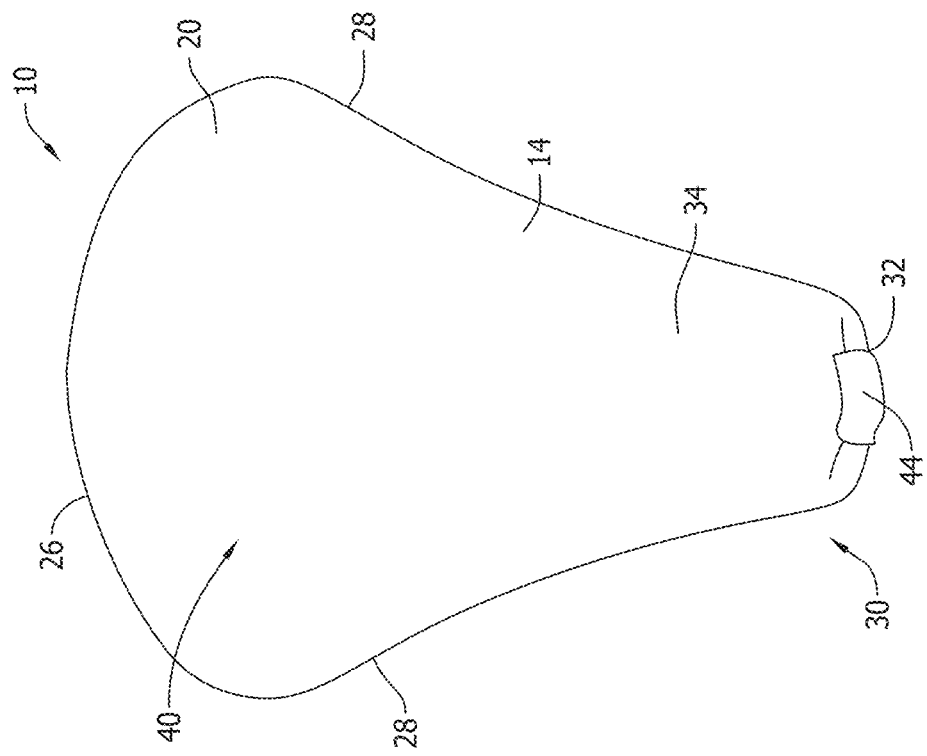
FIG. 5 is a back plan view of the male incontinence article seen in FIG. 4.
Figure 6:
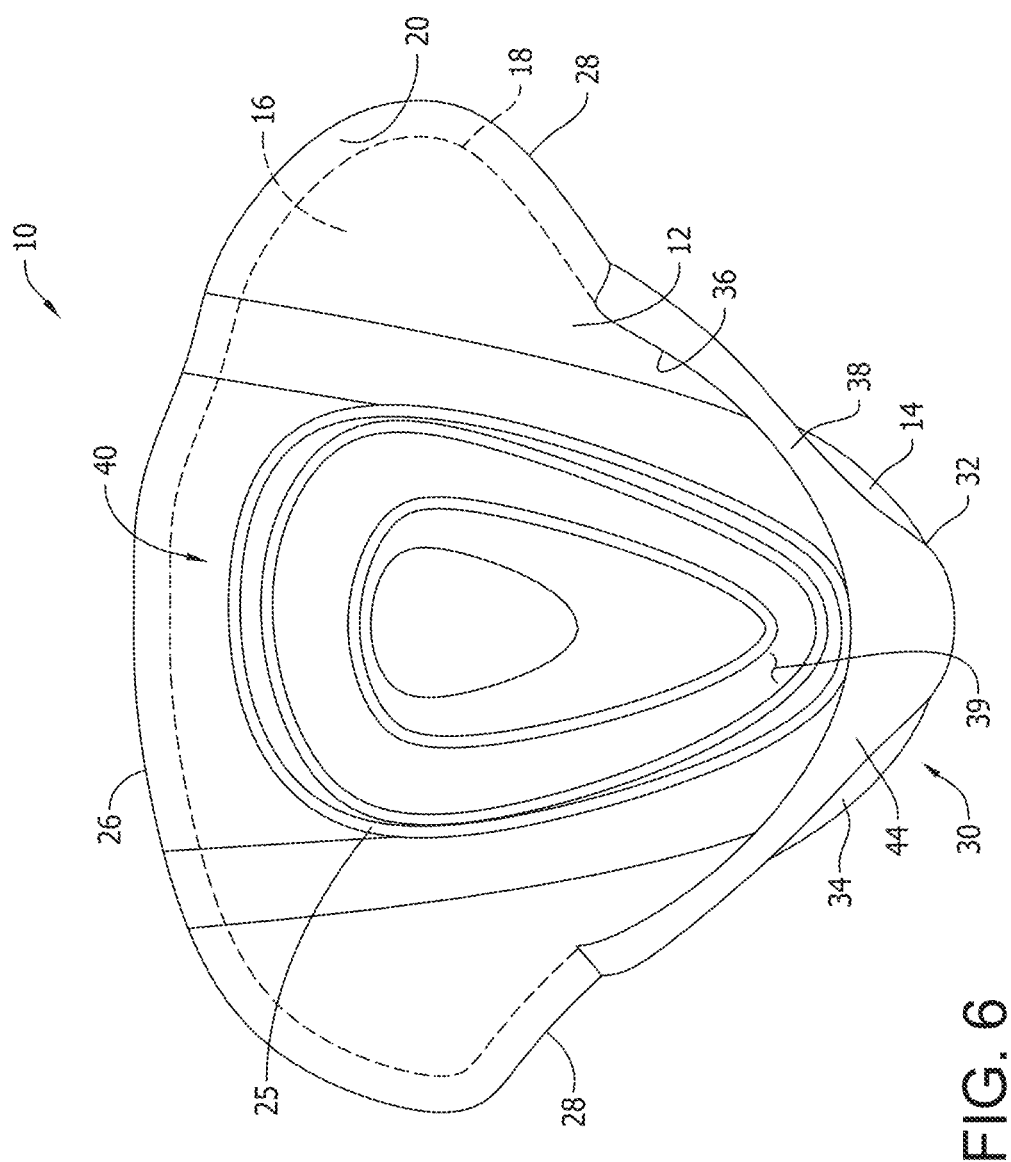
FIG. 6 is a top perspective of the male incontinence article seen in FIG. 4.

Referring now to the drawings and in particular to FIGS. 1-6, one suitable embodiment of a male incontinence article for use by a male is generally designated by reference numeral 10. FIGS. 1-3 illustrate the male incontinence article 10 in a laid flat configuration and FIGS. 4-6 illustrate the article in a use configuration. In one suitable embodiment, the article 10 is provided to the user in the use configuration. That is, the article 10 is provided (e.g., by the manufacturer) in the use configuration illustrated in FIGS. 4-6 such that the article is ready-for-use by the male user upon removal of the article from a suitable package and without requiring any manipulation of the article by the user prior to use. In another suitable embodiment, the article 10 is provided to the user in the laid flat configuration illustrated in FIGS. 1-3. In such an embodiment, the article 10 is adapted to be manually manipulated by the user to reconfigure the article from the laid flat configuration illustrated in FIGS. 1-3 to the use configuration illustrated in FIGS. 4-6. In such an embodiment, suitable fasteners (e.g., adhesive, tape, hook and loop, buttons, snaps) can be used to hold the article 10 in the use configuration.

As explained in more detail below, the male incontinence article 10 in its use configuration is suitably sized and shaped for receiving at least a portion of user's penis (i.e., at least the distal end of the user's penis having the urethra opening) and is adapted to take-in and retain fluids (e.g., urine, semen, sweat) discharged from the user's penis. The article 10 illustrated in FIGS. 1-6 is particularly adapted to take-in and retain urine associated with incontinence and, more specifically, light or mild incontinence.

In one suitable embodiment, the article 10 is configured to take-in and retain less than 300 grams of urine, and more specifically, less than 200 grams of urine, and even more specifically, less than 150 grams of urine. In another suitable embodiment, the male incontinence article 10 is configured to take-in and retain between 50 and 300 grams of urine, and more specifically, between 50 and 225 grams of urine, and even more specifically, between 50 and 150 grams of urine. It is understood, however, that the article 10 can be configured to take-in and retain more or even less urine without departing from some aspects of this disclosure. In other suitable embodiments wherein the article 10 is configured to take-in and retain more urine, for example, the article can be specifically configured for moderate or even severe incontinence.

The male incontinence article 10 seen in FIGS. 1-6 comprises a liquid permeable liner 12, a liquid impermeable outer cover 14, and an absorbent core 16 disposed between the liner and the over cover. A portion of the outer cover 14 is cut away in FIG. 2 to show the absorbent core 16. In addition, the absorbent core 16 can be seen relative to the liner 12 and the outer cover 14 in the cross-section provided in FIG. 3. As illustrated in FIGS. 1 and 2, the article 10 has a longitudinal direction 1 and a lateral direction 2. The lateral direction 2 and a z-direction 3 of the article 10 can be seen in FIG. 3.

The liquid permeable liner 12, which in the illustrated embodiment defines an interior surface of the article in the use configuration, is adapted to allow bodily fluids (e.g., urine) to pass through the liner and into the absorbent core 16. In one suitable embodiment, the liner 12 is configured to provide the user with a dry feeling by separating the absorbent core 16 and thus any discharged bodily fluids from the body, and specifically the penis, of the user.

Preferably, the liner 12 is comfortable, soft and nonirritating to the user's skin and can be formed from any suitable material or materials. For example, the liner 12 can include a woven fabric, a nonwoven fabric, a polymer film, a film-nonwoven fabric laminate or the like, as well as combinations thereof. Examples of suitable nonwoven fabrics for use in the liner 12 include airlaid nonwoven webs, spunbond nonwoven webs, meltblown nonwoven webs, bonded-carded webs, hydroentangled nonwoven webs, spunlace webs or the like, as well as combinations thereof. Other examples of suitable materials for constructing the liner 12, in whole or in part, include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the liner 12 is a film or a film laminate, the film would be apertured or otherwise treated to allow fluids, and specifically urine, to flow through the liner to the absorbent core 16.

Other examples of suitable materials for the liner 12 are composite materials of a polymer and a nonwoven fabric material. The composite materials are typically in the form of integral sheets generally formed by the extrusion of a polymer onto a nonwoven web, such as a spunbond material. In one embodiment, the liner 12 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner. The apertures or other openings can help increase the rate at which bodily liquids can move through the thickness of the liner and penetrate into the other components of the article (e.g., into the absorbent core 16). As mentioned above, the liner 12 of the illustrated embodiment is configured to direct bodily fluids, such as urine, away from the skin of the user and toward the absorbent core 16. Accordingly, in one suitable embodiment, the liner 12 retains little or no liquid in its structure during use of the article 10 thereby providing a relatively comfortable and nonirritating surface for direct contact with the penis of a user.

In the illustrated embodiment, for example, the liner 12 is a multicomponent liner having two or more different nonwoven or film materials, with the different materials placed in separate locations in the lateral direction 2 of the article 10. As seen in FIG. 1, the liner 12 can be a two layer or multicomponent material having a central portion 13 positioned along and straddling the longitudinal direction 1 of the article 10, with lateral side portions 15 flanking and bonded to each side edge of the central portion. The central portion 13 can be constructed from a first material and the side portions 15 can be constructed from a material which can be the same as or different from the material of the central portion. In such embodiments, the central portion 13 may be at least partially hydrophilic and the side portions 15 may be inherently hydrophobic or may be treated with a hydrophobic coating. Examples of constructions of multicomponent liners 12 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In some suitable embodiments, the central portion 13 of the liner 12 can be positioned symmetrically about the longitudinal axis of the article 10. Such central longitudinally directed central portion 13 can be a through-air-bonded-carded-web ("TABCW") having a basis weight between about 15 and about 100 gsm. Previously described nonwoven, woven, and apertured film liner materials may also be used. In various embodiments, the central portion 13 can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol of Pescara, Italy, and Tredegar of North Chesterfield, Va., U.S.A., may be utilized. Different nonwoven, woven, or film sheet materials may be utilized as the side portions 15 of the liner 12.

The selection of such liner materials can vary based upon the overall desired attributes of the liner 12. For example, it may be desired to have a hydrophilic material in the central portion 13 and hydrophobic-barrier type materials in the side portions 15 to prevent leakage and increase a sense of dryness in the area of the side portions. Such side portions 15 can be adhesively, thermally, ultrasonically, or otherwise bonded to the central portion 13 along or adjacent the longitudinally directed side edges of the central portion. Traditional absorbent article construction adhesive may be used to bond the side portions 15 to the central portion 13. Either of the central portion 13 and/or the side portions 15 may be treated with surfactants and/or skin-health benefit agents, as are well known in the art.

Such longitudinally directed side portions 15 can be of a single or multi-layered construction. In various embodiments, the side portions 15 can be adhesively or otherwise bonded laminates. In various embodiments, the side portions 15 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 1 and 15 gsm. When a film barrier layer is used in the overall liner 12 design, it may include opacifying agents, such as film pigments, that can help the film in masking stains along the article 10 side edges, thereby serving as a masking element. In such a fashion, the film layer can serve to limit visualization of a fluid insult stain along the article 10 side edges when viewed from above the liner 12. The film layer may also serve as a barrier layer to prevent rewet of the liner 12. In various embodiments, the side portions 15 can be laminates such as a spunbond-meltblown-meltblown-spunbond layer ("SMMS") laminate, spunbond-film laminate, or alternatively, other nonwoven laminate combinations. The central portion 13 of the liner 12 may be design to provide additional softness where the glans penis is most likely to contact the article 10 during use.

With reference now to FIGS. 2-5, the liquid impermeable outer cover 14, which in the illustrated embodiment defines the exterior surface of the article 10 in the use configuration, inhibits bodily fluid (e.g., urine) entering the absorbent core 16 from flowing through the entire article 10 and soiling a garment or undergarment being worn by a user. Suitable liquid impermeable outer cover 14 materials include, for example, a polymeric film, a woven fabric, a nonwoven fabric or the like, as well as combinations or composites thereof. In one suitable embodiment, the over cover 14 can operatively permit a sufficient passage of air and moisture vapor out of the article 10, and particularly out of the absorbent core 16, while blocking the passage of bodily fluids and odors often associated with such bodily fluids. An example of suitable materials for the outer cover 14 can include a breathable, microporous film, such as those described in, for example, U.S. Pat. No. 6,045,900 to Haffner et al., the entire disclosure of which is incorporated herein by reference.

With reference now to FIGS. 2 and 3, the absorbent core 16 of the article 10 contains one or more layers of absorbent materials. That is, the absorbent core 16 may be a single layer of absorbent materials or may be a multilayer structure. If the absorbent core 16 is a multilayer structure, each of the layers can contain similar materials or different materials. Suitable materials that can be used to form the absorbent core 16 include for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. The absorbent core 16 can also be formed from a composite comprised of a hydrophilic material that may be formed from various natural or synthetic fibers, wood pulp fibers, regenerated cellulose or cotton fibers, or a blend of pulp and other fibers. One particular example of a material which may be used as the absorbent core is an airlaid material.

In one suitable embodiment, the absorbent core 16 may also include a superabsorbent material, in addition to or in place of the hydrophilic material, which increases the ability of the absorbent core to absorb a large amount of fluid in relation to its own weight. Generally stated, the superabsorbent material can be a water-swellable, water-insoluble, hydrogel-forming polymeric absorbent material, which is capable of absorbing at least about 15 times, suitably about 30 times, and possibly about 60 times or more its weight in physiological saline (e.g., saline with 0.9 wt % NaCl). The superabsorbent materials can be inserted into the absorbent core 16 as particles, fibers, or in sheet form. The superabsorbent material may be biodegradable. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly cross-linked to render the material substantially water insoluble. Crosslinking may, for example, be by irradiation or covalent, ionic, Van der Waals, or hydrogen bonding. Hydroxyfunctional polymers have been found to be good superabsorbents for absorbent articles. Such superabsorbents are commercially available from Evonik Industries, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

In the illustrated embodiment and as illustrated in FIG. 3, for example, the absorbent core 16 comprises a coform upper layer 17 and a lower superabsorbent sheet 19 that underlies the upper layer. In one suitable embodiment, the superabsorbent sheet 19 is sized smaller in at least one of the longitudinal direction 1 and lateral direction 2 than the upper layer 17. That is, the superabsorbent sheet 19 can have a width and/or length that is less than a width and length of the upper layer 17. The width of the superabsorbent sheet 19 can be seen being less than the width of the upper layer 17 in FIG. 3.

Additional layers, including for example, a liquid acquisition and distribution layer (also referred to as a surge management or transfer layer), and/or a tissue or nonwoven wrap layer can be incorporated into the article. Neither the liquid acquisition and distribution layer nor the tissue layer is illustrated in the Figures. The liquid acquisition and distribution layer serves to temporarily hold an insulting fluid to allow the absorbent core 16 sufficient time to absorb the fluid, especially when a superabsorbent material is present. Typically, such liquid acquisition and distribution layers are placed between the liner 12 and the absorbent core 16. Suitable tissue layers are often used to wrap the absorbent core 16. Suitable liquid acquisition and distribution layers and the tissue or nonwoven wrap layers are readily known to those of ordinary skill in the art.

With reference again to FIGS. 1-3, the liner 12 and outer cover 14 of the illustrated embodiment are secured (i.e., bonded) together along their respective peripheral edges and outboard of the absorbent core 16. More specifically, both the liner 12 and the outer cover 14 extend beyond an outer peripheral edge 18 of the absorbent core 16 and are bonded together using any suitable bonding technique (e.g., adhesives, ultrasonic bonds, thermal bonds, pressure bonds, or combinations thereof) to define a bonded area 20. In one suitable embodiment, the absorbent core 16 can be bonded to the liner 12 and/or the outer cover 14. In another suitable embodiment, the absorbent core 16 is not bonded to either the liner 12 or the outer cover 14. Rather, the absorbent core 16 is captured between the liner 12 and the outer cover 14.

As seen in FIGS. 1 and 2, the illustrated male incontinence article 10 in the laid flat configuration has an upper portion 22 and a lower portion 24. The upper portion 22 includes an arcuate upper edge 26 and a pair of side edges 28 that taper inward to a respective transition 29 that separates the upper portion from the lower portion 24. The lower portion 24 includes a pair of side edges 31 that taper outward from the respective transition 29 to a generally arcuate lower edge 33. The lower portion 24 has a generally V-shaped cutout 35 that is aligned with a longitudinal axis of the article 10 and extends upward (as viewed in FIGS. 1 and 2) through the arcuate lower edge 33. It is understood that, in other suitable embodiments, the cutout 35 can have any suitable shape including, but not limited to, U-shaped, or semicircular. It is also understood that in some suitable embodiments, the cutout 35 can be omitted. In such an embodiment, the lower edge 33 of the lower portion 24 would be continuous instead of bifurcated as seen, e.g., in FIG. 1.

With reference again to FIGS. 1 and 2, the parts of the lower portion 24 adjacent the sides of the cutout 35 define lobes or ears 37 of the article 10 in the laid flat configuration. In the illustrated embodiment, each of the lobes 37 can be defined as the part of the lower portion 24 that is outboard from a straight line drawn between the apex of the cutout 35 and the respect transition 29. As a result, the remaining, central part of the lower portion 24 is generally triangular in shape. In one suitable embodiment, each of the lobes 37 has a surface area between about 3,500 mm² and about 10,500 mm² and, more suitably, between about 4,200 mm² and about 7,000 mm². In the illustrated embodiment, for example, each of the lobes 37 has a surface area of about 5,250 mm². In one suitable embodiment, the central, triangular part of the lower portion 24 has a surface area between about 3,000 mm² and about 9,000 mm² and, more suitably, between about 3,600 mm² and about 6,000 mm². In the illustrated embodiment, for example, each of the lobes 37 has a surface area of about 4,500 mm².

In the illustrated embodiment, the lobes 37 are substantially the same and are symmetrically positioned about the central triangular part along the article's central longitudinal axis. However, it is contemplated, that lobes 37 can have different sizes or shapes. It is also contemplates that the lobes 37 can be asymmetrical. In one such embodiment, one of the lobes 37 can be larger (i.e., have a greater surface area) than the other. It is further contemplated that one of the lobes 37 can be omitted. In such an embodiment, the single lobe 37 can have any suitable size and shape.

As illustrated in FIG. 1, the illustrated male incontinence article 10 in the laid flat configuration has a first, greatest length L1 that is defined as the longitudinal distance between longitudinally outermost extents of the article. In one suitable embodiment, the greatest length L1 of the article is in the range of about 100 mm to about 350 mm, and more suitably in the range of about 120 mm to about 200 mm. In the illustrated embodiment, for example, the absorbent article 10 has a greatest length L1 of about 190 mm. A greatest width W1 of the article 10, which in the illustrated embodiment is in the lower portion 24 of the article, is defined as the lateral distance between lateral outermost extents of the article. In one suitable embodiment, the greatest width W1 of the article 10 is in the range of about 120 mm to about 300 mm and more suitably about 150 mm to about 200 mm. In the illustrated embodiment, for example, the greatest width W1 of the article 10 is approximately 185 mm. It is understood that the absorbent article 10 can have any suitable greatest length L1 and any suitable greatest width W1 including lengths and widths different than those set forth above without departing from some aspects of this disclosure.

A second length L2 of the male incontinence article 10, which is aligned with the longitudinal axis of the article, is defined as the longitudinal distance between longitudinally extents of the article 10. That is, the second length L2 is simply the length of the article taken along the longitudinal axis of the article 10 in the laid flat configuration. In one suitable embodiment, the second length L2 of the article 10 is in the range of about 100 mm to about 200 mm and more suitably about 100 mm to about 180 mm. In the illustrated embodiment, for example, the absorbent article 10 has a second length L2 of about 160 mm. While in the illustrated embodiment, the greatest length L1 is greater than the second length L2, it is contemplated that, in other suitable embodiments, the greatest length and second length can be substantially equal.

A narrowest width W2 of the article 10, which is aligned with the transitions 29 between the upper portion 22 and lower portion 24, is defined as the lateral distance between lateral extents of the article disposed closest together in the lateral direction 2. In one suitable embodiment, the narrowest width W2 of the article 10 is in the range of about 75 mm to about 150 mm, and more suitably about 100 mm to about 175 mm. In the illustrated embodiment, for example, the narrowest width W2 is approximately 110 mm. It is understood that the absorbent article 10 can have any suitable second length L2 and any suitable narrowest width W2 including lengths and widths different than those set forth above without departing from some aspects of this disclosure.

In one suitable embodiment, a longitudinal distance Dl of the cutout 35 is in the range of about 0 mm to about 50 mm, and more suitably about 20 mm to about 40 mm. As one example, the distance Dl of the illustrated cutout 35 is approximately 30 mm. It is understood that the cutout 35 can have any suitable longitudinal distance Dl without departing from some aspects of this disclosure.

In one embodiment, a total or maximum thickness T of the male incontinence article 10 is suitably in the range of about 1 mm to about 15 mm, and more suitably about 3 mm to about 6 mm (FIG. 3). As one example, the thickness of the illustrated article 10 is approximately 4 mm. It is understood, however, that the thickness may be other than as set forth above.

In one suitable embodiment, each side of the male incontinence article 10 (i.e., the side comprising the liner 12 (FIG. 1) and the side comprising the outer cover 14 (FIG. 2)) has a total surface area in the range of about 15,000 mm² to about 45,000 mm², and more suitably about 19,000 mm² to about 30,000 mm². In the illustrated embodiment, for example, both sides of the male incontinence article 10 has a surface area of about 24,000 mm².

As seen in FIG. 1, the surface area in the lower portion 24 of the illustrated male incontinence article 10 is greater than the surface area in the upper portion 22 of the article. Suitably, the lower portion 24 of the article 10 has a surface area in the range of about 10,000 mm² to about 30,000 mm², and more suitably about 12,000 mm² to about 20,000 mm². In the illustrated embodiment, for example, the lower portion 24 has a surface area of about 15,000 mm². Suitably, the upper portion 22 of the article 10 has a surface area in the range of about 5,000 mm² to about 15,000 mm², and more suitably about 7,000 mm² to about 10,000 mm². In the illustrated embodiment, for example, the upper portion 22 has a surface area of about 9,000 mm².

It is contemplated that other suitable shapes and/or sizes for the article 10 in its laid flat configuration can be used, provided that the shape and size of the article will allow it to be configured to its use configuration (FIGS. 4-6).

In one suitable embodiment and as seen in FIGS. 1, 3, and 5, an aesthetic feature or visual cue 25 is visible through or is disposed on the liner 12 to assist the user in either properly aligning the article 10 during use or highlighting regions. In the illustrated embodiment, for example, the visual cue comprises printing including an ovate alignment aid surrounded by a plurality of elliptical rings. During use, the user can align his penis with the ovate alignment aid when inserting his penis into the article. It is contemplated that other suitable visual cues can be provided on the article 10.

With reference now to FIGS. 4-6, the male incontinence article 10 is illustrated in its use configuration. Thus, either the user was provided the article 10 in the use configuration upon removal of the article from a suitable package or the user manually manipulated the article from the laid flat configuration illustrated in FIGS. 1-3 to the use configuration illustrated in FIGS. 4-6. FIG. 4 is a front perspective of the male incontinence article 10 illustrating the body-facing side of the article. That is, during use of the article 10, the side of the article seen in FIG. 4 is adapted to face and to be in at least partial engagement with the skin of the user. FIG.

5 is a back plan view of the male incontinence article 10 illustrating the garment facing side of the article. In other words, FIG. 5 illustrates the portion of the article 10 that faces away from the user during use.

As seen in FIGS. 4 and 6, the lower portion 24 of the article 10 is configured to define an absorbent cup or pocket, indicated generally at 30, that is sized and shaped to receive at least the distal end of the user's penis having the urethra opening. As best seen in FIG. 4, the cup 30 has a closed bottom 32, a sidewall 34 extending upward from the closed bottom, and an open top 36 defined by an upper edge 38 of the sidewall. As seen in FIG. 6, the closed bottom 32 and the sidewall 34 cooperatively define an interior chamber 39 of the cup adapted to receive at least a portion of the user's penis. In the use configuration, the lobes 37 seen in FIGS. 1 and 2 are moved out of plane with the upper portion 22 and overlapped or otherwise positioned adjacent each other (e.g., in abutting relationship) to form the cup 30.

In one suitable embodiment, the volume of the interior chamber 39 is between about 50 cm$^3$ and about 600 cm$^3$, and more specifically between about 100 cm$^3$ and about 300 cm$^3$. In the illustrated embodiment, for example, the interior chamber 39 has a volume of about 150 cm$^3$. In another suitable embodiment, the interior chamber 39 can have a volume of about 75 cm$^3$. It is understood that, in other suitable embodiments, the interior chamber 39 can have any suitable volume. In the illustrated embodiment, the sidewall 34 tapers outward from the closed bottom 32 to the open top 36 such that the sidewall has greater width (or diameter) adjacent the open top as compared to the width (or diameter) of the sidewall adjacent the closed bottom. As a result, the sidewall 34 of the illustrated cup 30 is generally a frustum and, more specifically, a truncated cone. It is contemplated that the sidewall 34 of the cup 30 can have any suitable shape (e.g., cylindrical) without departing from some aspects of this disclosure.

With reference again to FIG. 4, the upper portion 22 of the male incontinence article 10 defines an upstanding wall, indicated generally at 40, that extends upward from the cup 30. More specifically, the upstanding wall 40 extends upward from and thus is a continuation of a portion of the upper edge 38 of the sidewall 34. As seen in FIG. 4, the upper edge 38 of the sidewall 34 has a generally annular or elliptical circumference and the upstanding wall 40, in the illustrated embodiment, extends along less than 60 percent of the circumference. In one suitable embodiment, the upstanding wall 40 extends along between about 30 percent and about 60 percent of the circumference of the upper edge 38 of the sidewall 34 and, more preferably, between about 40 percent and about 50 percent. In the illustrated embodiment, for example, the upstanding wall 40 extends along about 45 percent of the upper edge 38 of the sidewall 34.

As a result, a significant portion (i.e., more than 50 percent) of the upper edge 38 of the sidewall 34 of the cup 30 is free of the upstanding wall 40. In one suitable embodiment and as illustrated in FIG. 4, the portion of the upper edge 38 of the sidewall 34 of the cup 30 that is free of the upstanding wall 40 is concave relative to a plane extending in the lateral direction 2. More specifically, the cup 30 has a first height H1 at locations where the upstanding wall 40 is present, and a second height H2 spaced from the upstanding wall that is less than the first height. In the illustrated embodiment, the second height H2 is generally aligned with the longitudinal axis of the article 10 in the use configuration. It is contemplated that in other suitable embodiments, the cup 30 can have a constant height such that the first height H1 is generally equal to the second height H2. In one suitable embodiment, the first height H1 and the second height H2 are in a range between about 60 mm and about 120 mm and, more suitably, between about 80 mm and about 100 mm. In the illustrated embodiment, for example, the first height H1 is approximately 90 mm and the second height H2 is approximately 75 mm.

As seen in FIG. 4, the upstanding wall 40 of the use configuration corresponds to the upper portion 24 of the article 10 in its laid flat configuration (FIGS. 1 and 2). Thus, the upstanding wall 40 includes the arcuate upper edge 26 and the pair of inwardly tapering side edges 28. In use, the upstanding wall 40 of the illustrated embodiment of the male incontinence article 10 is generally arcuate as it extends about the upper edge 38 of the sidewall 34 of the cup 30. It is contemplated that the upstanding wall may flatten out (become more planer and less arcuate) as the upstanding wall 40 extends longitudinally away from the cup 30 (FIG. 6). In other words, the upstanding wall 40 may be more flat adjacent its upper edge 26 compared to the portion of the upstanding wall adjacent the cup 30. This flattened area can allow for attachment to the underwear without deforming the shape of the cup 30 and sit flush against or adjacent to the user's pelvic bone.

With reference yet again to FIG. 4, the cup 30 of the illustrated article 10 includes a seam 42 extending in the longitudinal direction 1 the entire height of the sidewall 34. In the illustrated embodiment, for example, the seam 42 is a fin seam but it is understood that the seam can be any suitable type of seam including, but not limited to, a butt seam or a lap seam. Suitably, the seam 42 is aligned with the longitudinal axis of the article 10. In the illustrated embodiment, the seam 42 extends along the second height H2 thus the seam is the shortest possible length while still extending the entire height of the sidewall 34. It is contemplated that the seam 42 can be positioned at different locations on the article 10.

In one suitable embodiment and as seen best in FIG. 4, the seam 42 and the upper edge 38 of the sidewall 34 of the cup 30 is covered by a suitable covering material 44 to prevent the seam and upper edge from coming into direct contact with the user's skin during use of the male incontinence article 10. Accordingly, the seam 42 and the upper edge 38 do not contact the user's skin during use of the article. It is contemplated that in some embodiments of the article 10, the covering material 44 can be omitted or can cover more of the article than seen in FIG. 4. The covering material 44 can be omitted in one suitable embodiment wherein the seam 42 is nonirritating or treated to be nonirritating to the user or is positioned such that the seam would not come into contact with the user during use. In another suitable embodiment, the cover material 44 can be extended to line at least a portion of the interior chamber 39 of the cup 30.

While any suitable material can be used for the cover material 44, one example of a suitable material includes a through-air-bonded-carded-web ("TABCW") having a basis weight between about 15 and about 100 gsm. Previously described nonwoven, woven, and apertured film liner materials may also be used. In various embodiments, the cover material 44 can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol of Pescara, Italy, and Tredegar of North Chesterfield, Va., U.S.A., may be utilized.

Figure 7:
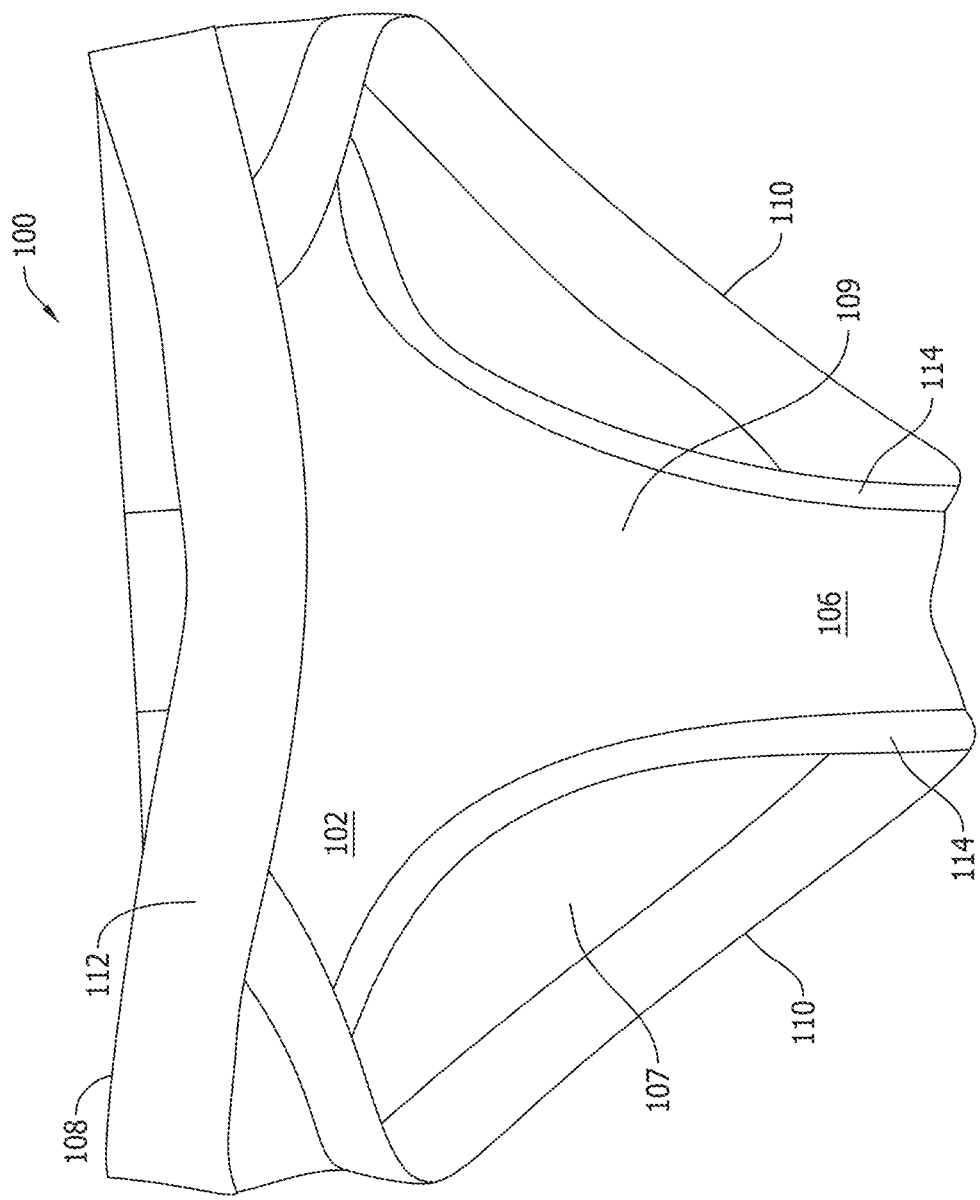
FIG. 7 is a front plan view of underwear in the form of an underwear brief for use with the male incontinence article.
Figure 8:
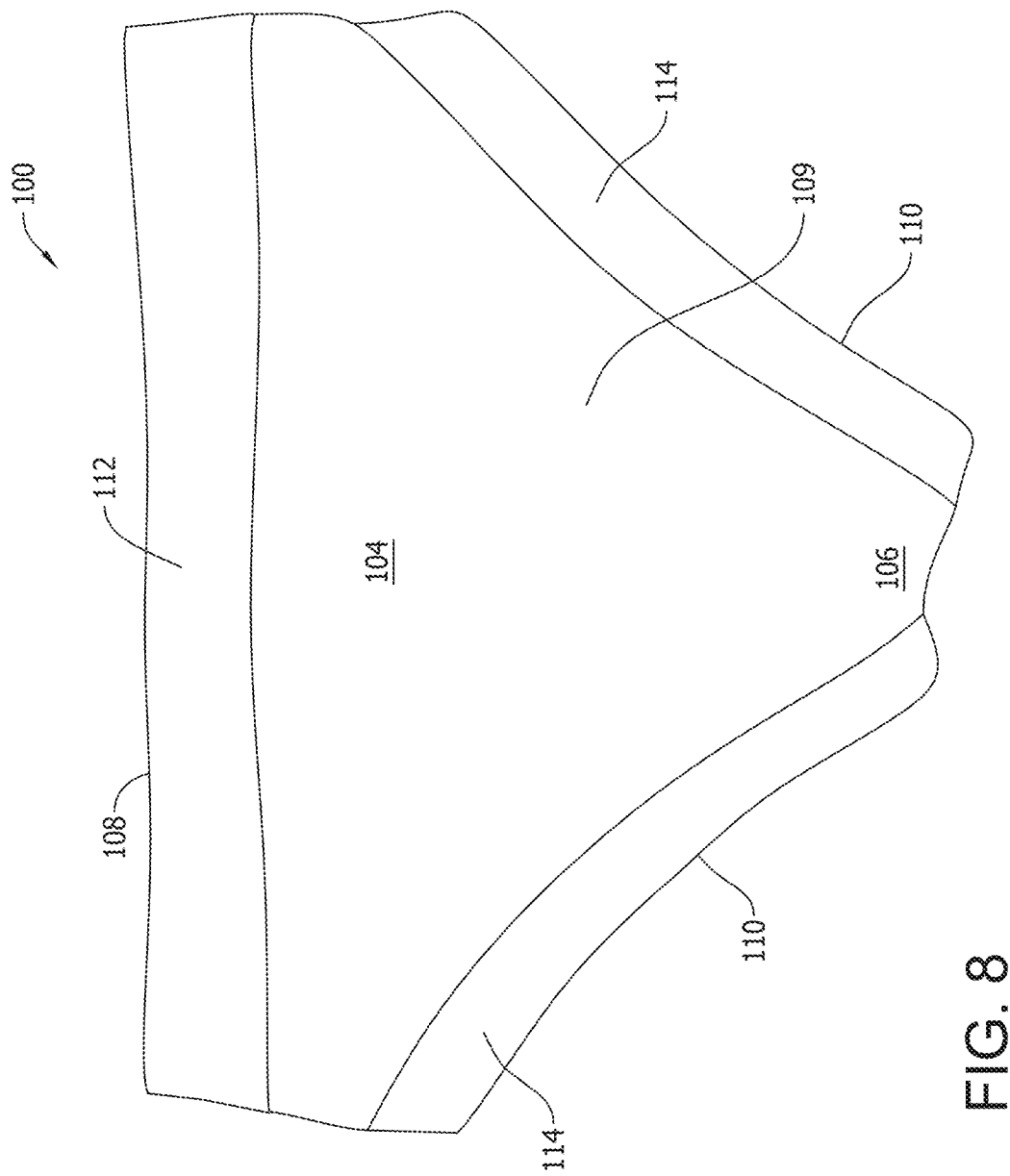
FIG. 8 is a back plan view of the underwear of FIG. 7.
Figure 9:
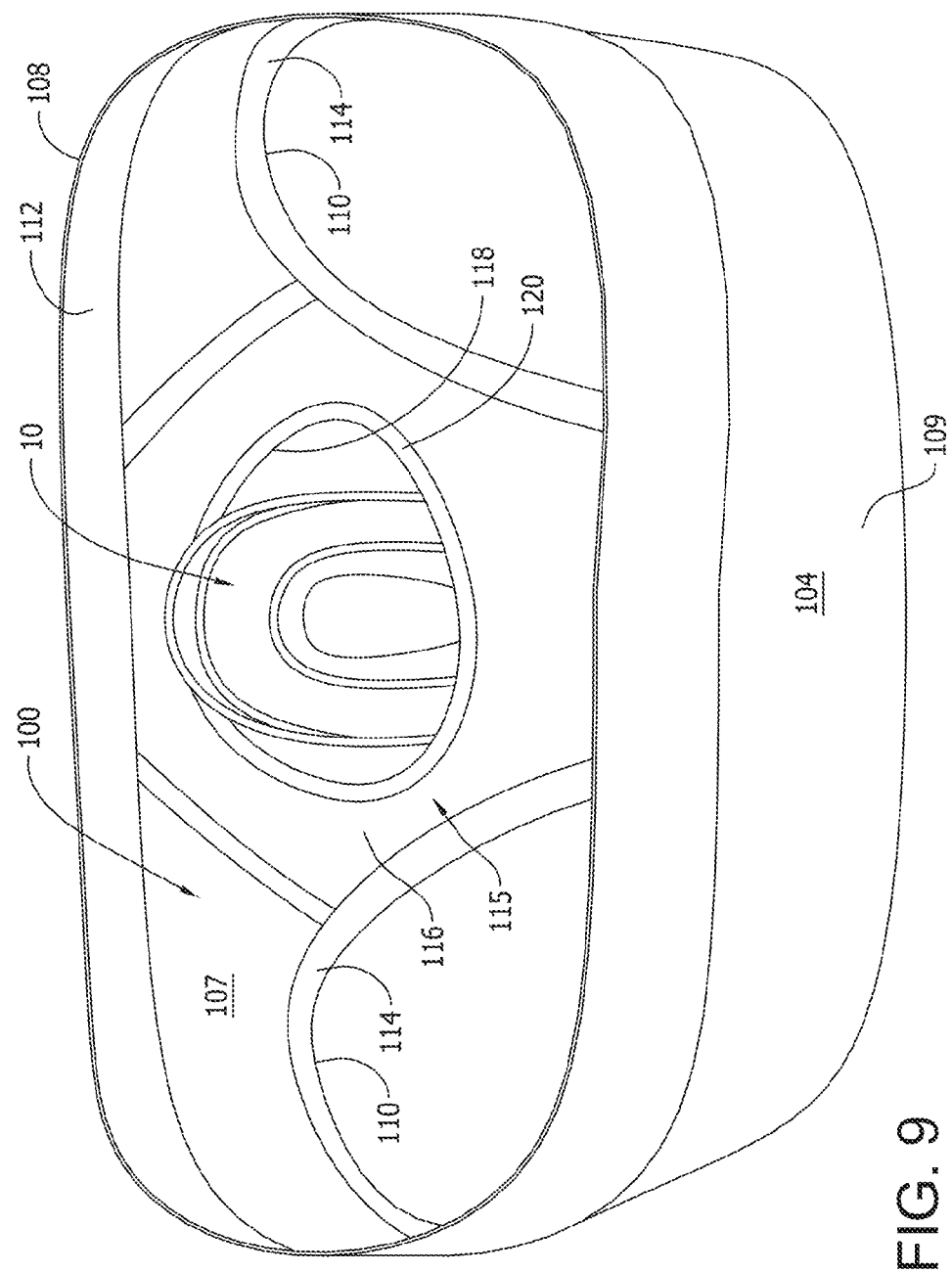
FIG. 9 is a top perspective of the underwear showing an interior pocket having the male incontinence article therein.

With reference now to FIGS. 7-9, a male brief style underwear for use with the article 10 of FIGS. 1-6 is indicated generally at 100. As seen in FIGS. 7 and 8, the underwear 100 comprises a front waist region 102, a back waist region 104, a crotch region 106 extending longitudinally between and interconnecting the front and back waist regions, an interior, body-facing surface 107, and an exterior, garment-facing surface 109. The front waist, back waist, and crotch regions 102, 104, 106 collectively define a waist opening 108 and a pair of leg openings 110. A suitable waist elastic 112 extends circumferentially about the waist opening 108, and suitable leg elastics 114 extend circumferentially about each of the leg openings 110.

As seen in FIG. 9, the front waist region 102 includes an interior pocket, indicated generally at 115, sized and shaped for receiving one of the male incontinence articles 10 illustrated in FIGS. 1-6. More specifically, the front waist region 102 of the underwear 100 includes an interior panel 116 that, in the illustrated embodiment, extends between and is secured (e.g., sewn) to the waist elastic 112 and each of the leg elastics 114. The panel 116 includes a generally circular or elliptical opening 118 disposed below the waist elastic 112. The portion of panel 116 defining the opening 118 is trimmed or edged with suitable trimming material 120. The opening 118 is sized and shaped for allowing one of the articles 10 to be inserted through the opening and into the space between the interior panel 116 and the front waist region 102.

Figure 10:
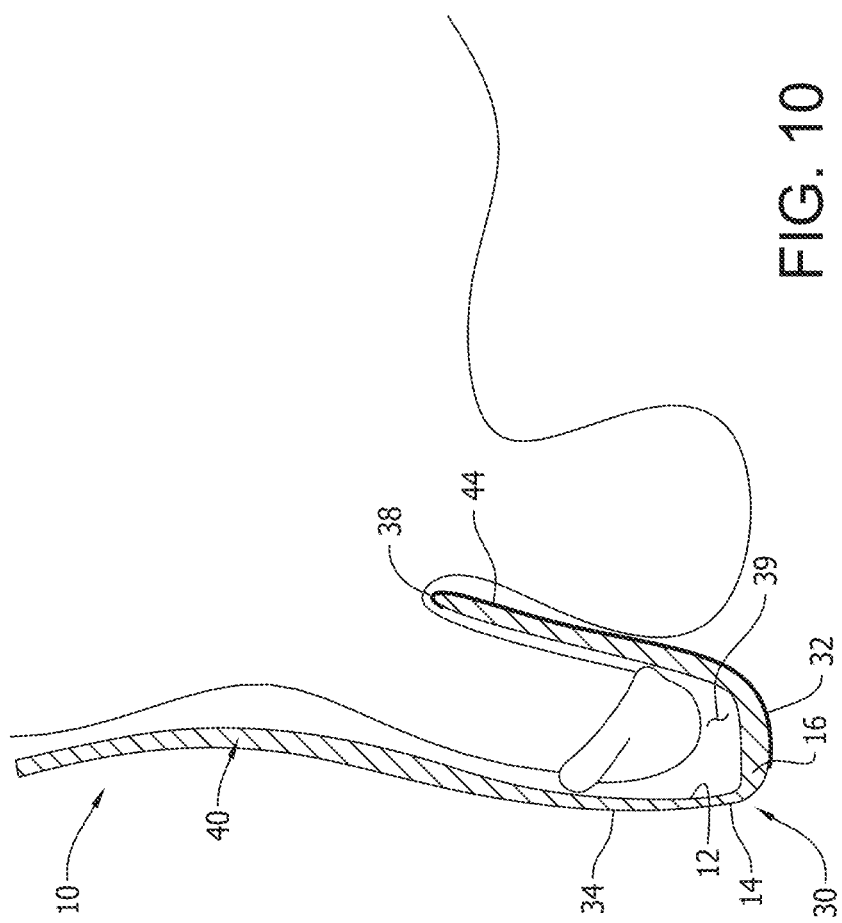
FIG. 10 is a cross-section of the article of FIG. 4 shown positioned relative to the male anatomy during use.

During use, the user dons the underwear 100 in a conventional manner such that his legs extend through the leg openings 110 so that the leg elastic 114 circumscribes his thighs and the waist elastic 112 about the waist opening 108 circumscribes his waist. The user is able to manipulate the underwear 100 (e.g., pull outward, pull down, take off) and insert one of the male incontinence articles 10 into the pocket 115 in the underwear through the opening 118. The user then positions his penis such that the base of the shaft (i.e., the portion of the shaft adjacent the scrotum) of the penis rest on or is in close proximity to the upper edge 38 of the sidewall 34 of the cup 30 such that the majority of the user's penis is inserted into the interior chamber 39 of the cup 30 (FIG. 10). Thus, during use of the article 10, at least a portion of the penis of the user is fully surrounded by the cup (e.g., the sidewall 34 and the closed bottom 32). However, the cup 30 does not constrict or otherwise conform to the penis. In the illustrated embodiment, the scrotum of the user remains outside the interior chamber 39 of the cup 30 during use but it is contemplated that, in other suitable embodiments, the article and specifically the cup can be adapted to receive the scrotum as well as the user's penis.

Once the male incontinence article 10 is secured within the underwear 100 and the user's penis properly positioned in the interior chamber 39 of the cup 30, the user can don the underwear in a conventional manner. The article 10 is adapted to keep the user's penis within the interior chamber 39 of the cup 30 during use. More specifically, during use, the user's penis is captured by the sidewall 34 and the closed bottom 32 of the cup 30 to inhibit the user's penis from withdrawing from the interior chamber 39 during movement (e.g., walking, running, bending, sitting, stretching) by the user.

The user can readily change the male incontinence article 10 by manipulating the underwear 100 (e.g., pull outward, pull down, take off) and withdrawing the used male incontinence article 10 from the pocket 115 and inserting a new article therein. The used article 10 can be readily disposed of. In the illustrated embodiment, the underwear can be laundered for reuse. That is, in the illustrated embodiment, the article 10 is disposable while the underwear is reusable. It is contemplated, however, that the underwear 100 could be disposable.

Figure 11:
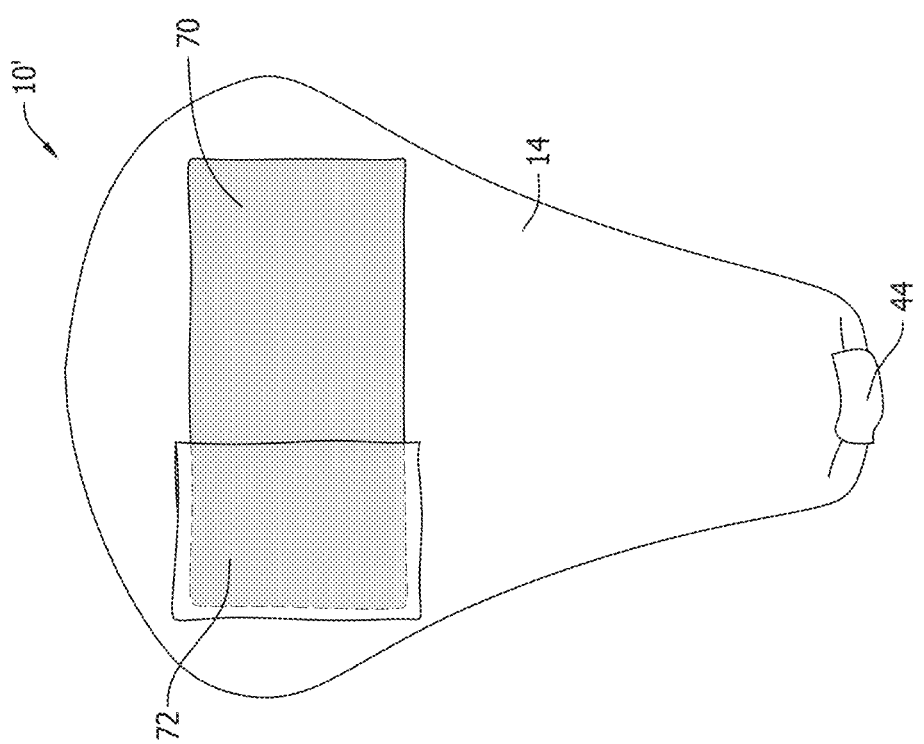
FIG. 11 is a back plan view of another suitable embodiment of a male incontinence article having adhesive thereon.
Figure 12:
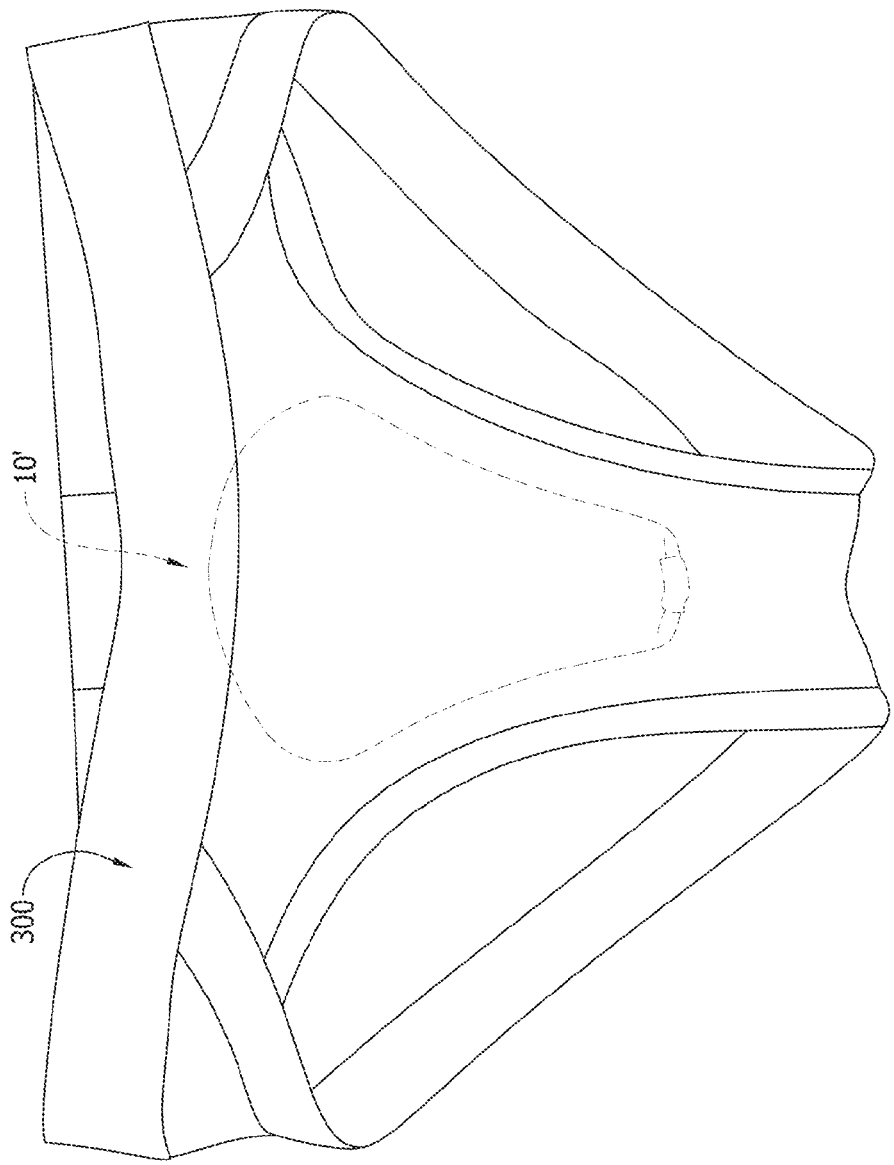
FIG. 12 is a plan view illustrating the male incontinence article of FIG. 10 adhered to conventional underwear.

FIGS. 11 and 12 illustrate another suitable embodiment of a male incontinence article, indicated generally at 10', in accordance with this disclosure. The article 10' seen in FIGS. 11 and 12 is substantially the same as the article 10 seen in FIGS. 1-6 except that a suitable adhesive 70 (broadly, "attachment element") is provided on the outer cover 14 of the article 10' for adhering the article to an overlying garment (e.g., underwear). In the illustrated embodiment, the adhesive 70 is provided in a single strip extending in the lateral direction 2 but it is understood that the adhesive can have any suitable configuration and applied in any suitable amounts.

Suitably, the adhesive 70 is covered with a selectively removable peel strip 72 until the user is ready to adhere the article to the garment. For example, the article 10' is illustrated being adhered using the adhesive 70 to conventional underwear, indicated generally at 300, in FIG. 11. It is contemplated that other suitable types of attachment elements besides adhesive 70 can be used to secure the article 10' to the underwear 300. For example, other types of suitable attachment elements include, but are not limited to, hook and loop fasteners, snaps, and buttons. It is also contemplated that the article 10' can include suitable body adhesive (not shown) for adhering the article to the user instead of or in addition to the adhesive 70 used to adhere the article to the user's underwear 300.

Figure 13:
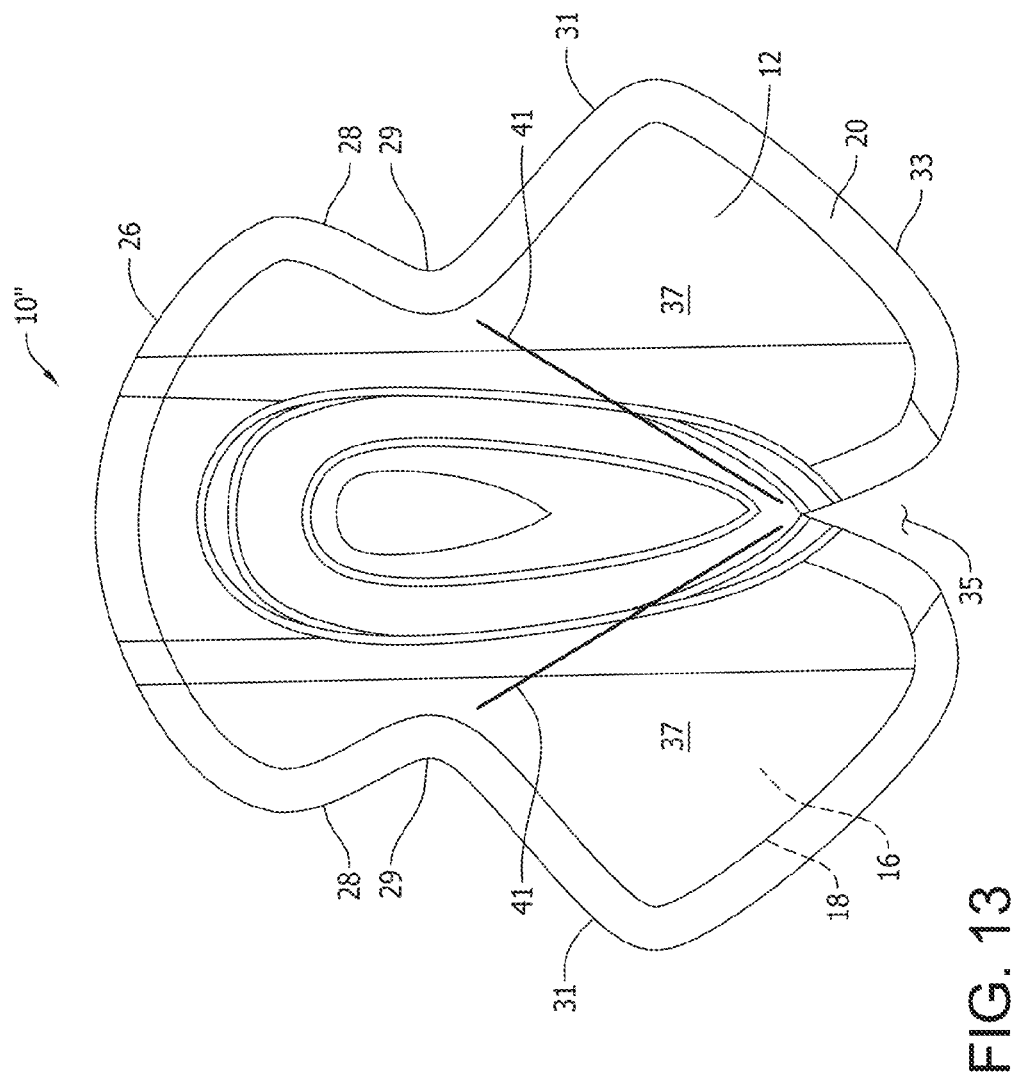
FIG. 13 is a front plan view of another suitable embodiment of a male incontinence article in a laid flat configuration showing a liquid permeable liner of the article.
Figure 14:
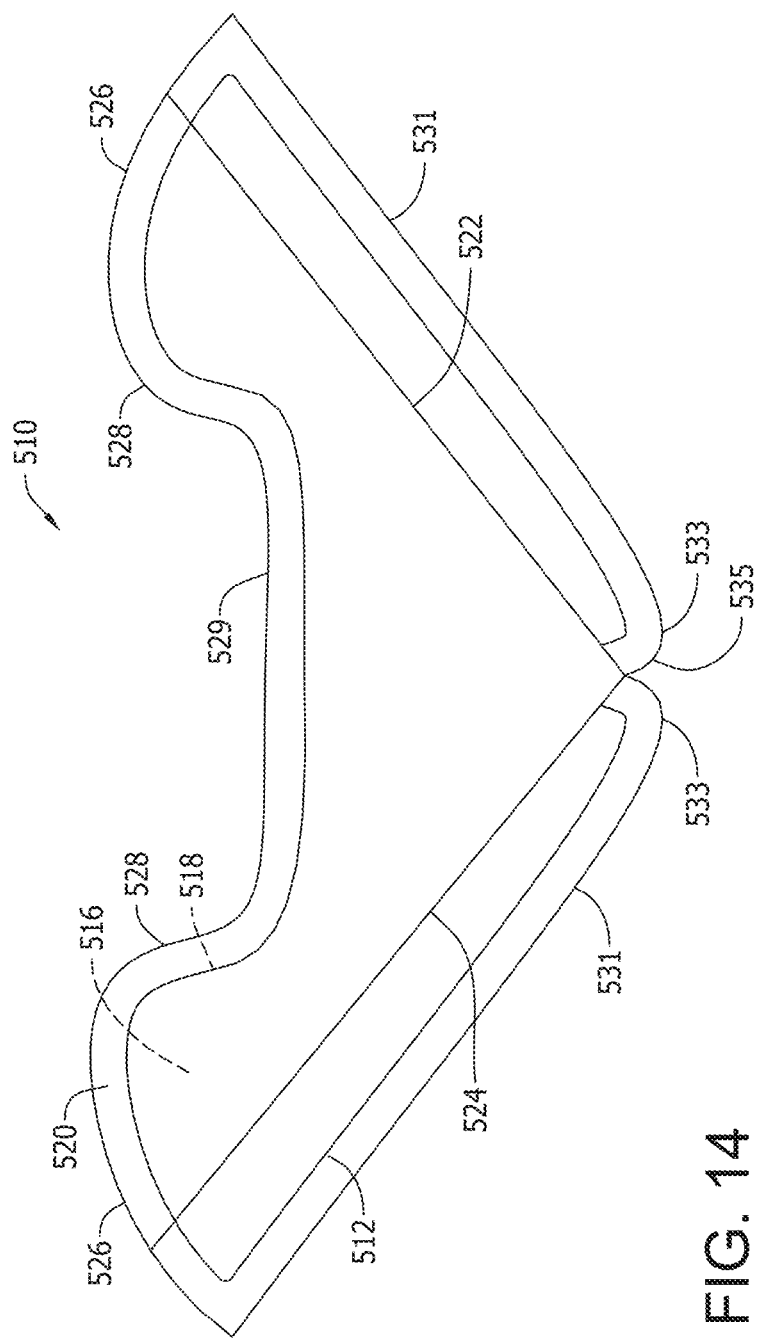
FIG. 14 is a front plan view of another suitable embodiment of a male incontinence article in a laid flat configuration showing a liquid permeable liner of the article.
Figure 15:
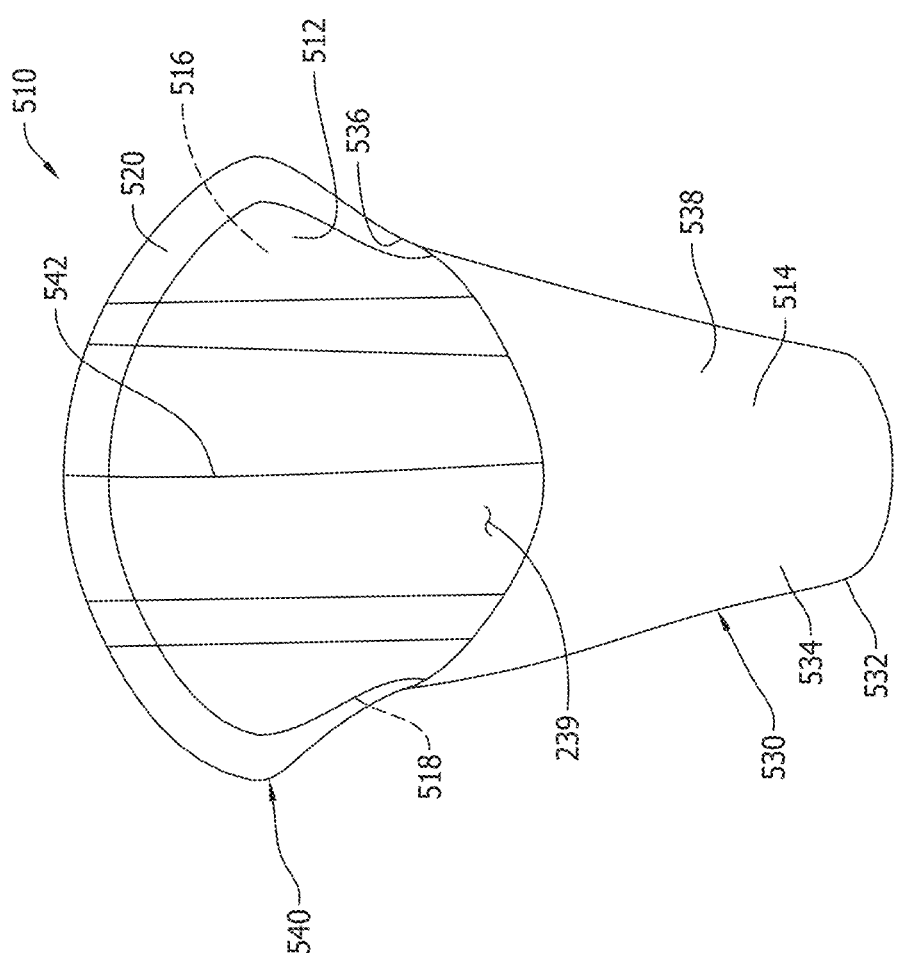
FIG. 15 is a front perspective of a male incontinence article similar to the one illustrated in FIG. 1 in a use configuration wherein the article is positioned to define a cup and an upstanding wall extending from the cup.

FIG. 13 illustrates another suitable embodiment of a male incontinence article, indicated generally at 10", in accordance with this disclosure. The article 10" seen in FIG. 13 is substantially the same as the article 10 seen in FIGS. 1-6 except that forming elements 41 are provided adjacent each of the lobes 37. The forming elements 41 facilitate moving the lobes 37 out of plane with the upper portion 22 to form the cup 30 and can include, for example, a gap in the absorbent core 16, an embossing line or other line of weakness. It is contemplated that the lobes 37 can be formed integrally with the central triangular section as illustrated in FIG. 13 or as separate pieces and attached to the article 10 using any suitable attachment (e.g., bonding, tape strips). When using tape strips to attach the lobes 37 to the article 10, the tape strips define the forming elements 41. FIGS. 14 and 15 illustrate yet another suitable embodiment of a male incontinence article, indicated generally at 510, in accordance with this disclosure. FIG. 14 illustrates the male incontinence article 510 in a laid flat configuration and FIG. 15 illustrates the article in a use configuration. In one suitable embodiment, the article 510 is provided to the user in the use configuration. That is, the article 510 is provided (e.g., by the manufacturer) in the use configuration illustrated in FIG. 15 such that the article is ready-for-use by the male user upon removal of the article from a suitable package and without requiring any manipulation of the article by the user prior to use.

In another suitable embodiment, the article 510 is provided to the user in the laid flat configuration illustrated in FIG. 14. In such an embodiment, the article 510 is adapted to be manually manipulated by the user to reconfigure the article from the laid flat configuration illustrated in FIG. 14 to the use configuration illustrated in FIG. 15. In such an embodiment, suitable fasteners (e.g., adhesive, tape, hook and loop, buttons, snaps) can be used to hold the article 510 in the use configuration.

As explained in more detail below, the male incontinence article 510 in its use configuration is suitably sized and shaped for receiving at least a portion of user's penis (i.e., at least the distal end of the user's penis having the urethra opening) and is adapted to take-in and retain fluids (e.g., urine, semen, sweat) discharged from the user's penis. The article 510 illustrated in FIGS. 14 and 15 is particularly adapted to take-in and retain urine associated with incontinence.

The male incontinence article 510 seen in FIGS. 14 and 15 comprises a liquid permeable liner 512, a liquid impermeable outer cover 514, and an absorbent core 516 disposed between the liner and the over cover. The liner 512, outer cover 514, and absorbent core 516 are substantially the same as the liner 12, outer cover 14, and absorbent core 16 described above with respect to FIGS. 1-6.

The liner 512 and outer cover 514 of the illustrated embodiment are secured (i.e., bonded) together along their respective peripheral edges and outboard of the absorbent core 516. More specifically, both the liner 512 and the outer cover 514 extend beyond an outer peripheral edge 518 of the absorbent core 516 and are bonded together using any suitable bonding technique (e.g., adhesives, ultrasonic bonds, thermal bonds, pressure bonds, or combinations thereof) to define a bonded area 520. In one suitable embodiment, the absorbent core 516 can be bonded to the liner 512 and/or the outer cover 514. In another suitable embodiment, the absorbent core 516 is not bonded to either the liner 512 or the outer cover 514. Rather, the absorbent core 516 is captured between the liner 512 and the outer cover 514. The illustrated male incontinence article 510, in the laid flat configuration, is symmetric about the longitudinal axis of the article. Thus, the article 510 illustrated in FIG. 14 has a first portion 522 (or right-side portion as viewed in FIG. 14) and a second portion 524 (or left-side portion as viewed in FIG. 14). Both the first and second portions 522, 524 have an arcuate upper edge 526 and a pair of tapered edges 528 that taper inward to a common edge 529 that extends between the first portion 522 and the second portion 524. In the illustrated embodiment, the common edge 529 is generally straight. It is contemplated, however, that the common edge 529 can be other than straight (e.g., curved) in other suitable embodiments.

Each of the first and second portions 522, 524 include side edges 531 that taper inward from the respective upper edge 526 to a generally arcuate (or semicircular) lower edge 533. The lower edge 533 has a generally V-shaped cutout 535 that is aligned with the longitudinal axis of the article 510 and extends upward (as viewed in FIG. 14) through the lower edge 533. It is understood that, in other suitable embodiments, the cutout 535 can have any suitable shape including, but not limited to, U-shaped, and semicircular. It is also understood that in some suitable embodiments, the cutout 535 can be omitted.

With reference now to FIG. 15, the male incontinence article 510 is illustrated in its use configuration. Thus, either the user was provided the article 510 in the use configuration upon removal of the article from a suitable package or the user manually manipulated the article from the laid flat configuration illustrated in FIG. 14 to the use configuration illustrated in FIG. 15. FIG. 15 is a front perspective of the male incontinence article 510 illustrating the body-facing side of the article. That is, during use of the article 510, the side of the article seen in FIG. 15 is adapted to face and to be in at least partial engagement with the skin of the user. The opposite side of the article 510 is the garment facing side or the portion of the article that faces away from the user during use.

As seen in FIG. 15, the article, in its use configuration, comprises an absorbent cup or pocket, indicated generally at 530, that is sized and shaped to receive at least the distal end of the user's penis having the urethra opening. The cup 530 has a closed bottom 532, a sidewall 534 extending upward from the closed bottom, and an open top 536 defined by an upper edge 538 of the sidewall. The closed bottom 532 and the sidewall 534 cooperatively define an interior chamber 539 of the cup adapted to receive at least a portion of the user's penis.

In the illustrated embodiment, the sidewall 534 tapers outward from the closed bottom 532 to the open top 536 such that the sidewall has greater width (or diameter) adjacent the open top as compared to the width (or diameter) of the sidewall adjacent the closed bottom. As a result, the sidewall 534 of the illustrated cup 530 is generally a frustum and, more specifically, a truncated cone. It is contemplated that the sidewall 534 of the cup 530 can have any suitable shape (e.g., cylindrical) without departing from some aspects of this disclosure.

In the use configuration, the sides edges 531 seen in FIG. 14 are overlapped with each other or otherwise positioned adjacent each other (e.g., in abutting relationship) to define the cup 530 and an upstanding wall, indicated generally at 540, that extends upward from the cup. More specifically, the upstanding wall 540 extends upward from and thus is a continuation of a portion of the upper edge 538 of the sidewall 534. As seen in FIG. 15, the upper edge 538 of the sidewall 534 has a generally annular or elliptical circumference and the upstanding wall 540, in the illustrated embodiment, extends along less than 50 percent of the circumference. In one suitable embodiment, the upstanding wall 540 extends along between about 30 percent and about 60 percent of the circumference of the upper edge 38 of the sidewall 34 and, more preferably, between about 40 percent and about 50 percent. In the illustrated embodiment, for example, the upstanding wall 540 extends along about 45 percent of the upper edge 538 of the sidewall 534.

The illustrated article 510 includes a seam 542 extending in the longitudinal direction 1 the entire height of the upstanding wall 540. In the illustrated embodiment, for example, the seam 542 is a fin seam but it is understood that the seam can be any suitable type of seam including, but not limited to, a butt seam or a lap seam. Suitably, the seam 542 is aligned with the longitudinal axis of the article 510. In the illustrated embodiment, the seam 542 is spaced from and faces away from the user during use of the male incontinence article 510.

Figure 16:
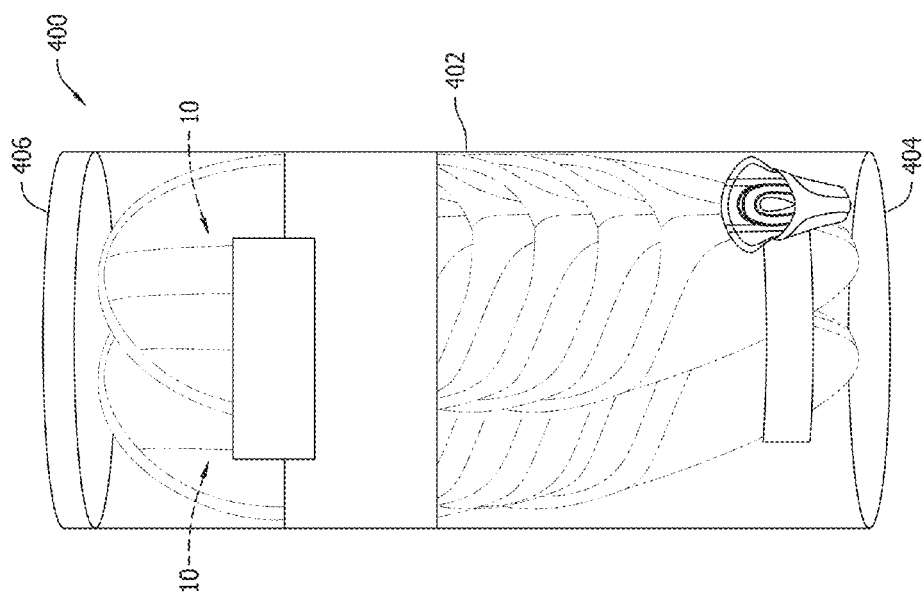
FIG. 16 is a front plan view of one suitable embodiment of a package containing a plurality of the male incontinence articles.
Figure 17:
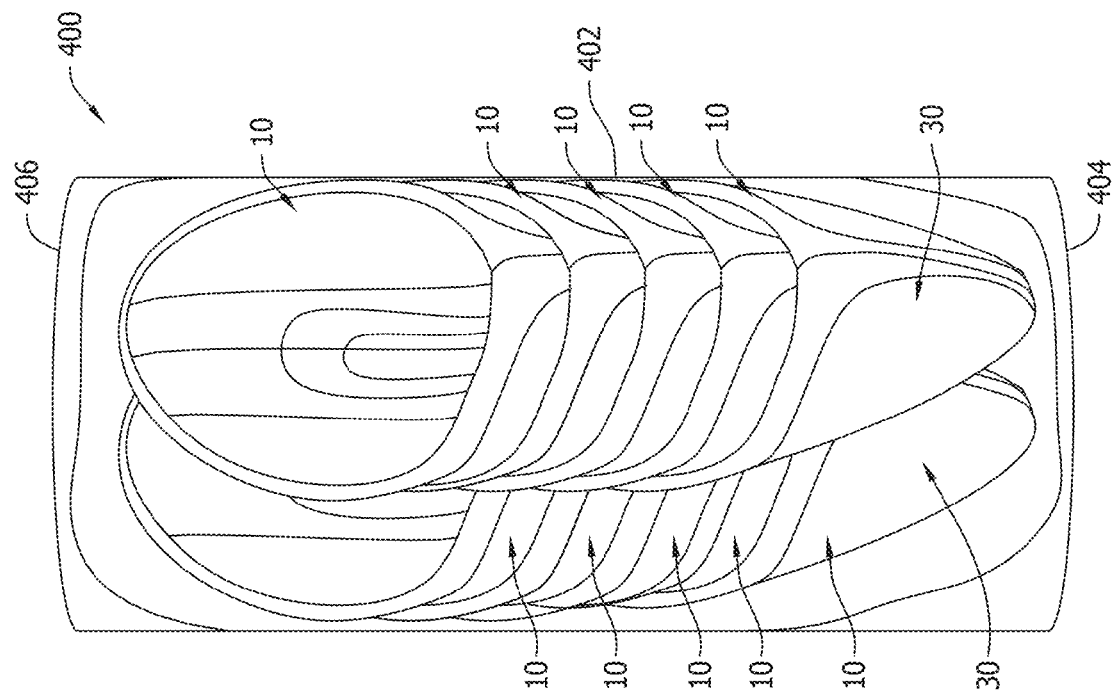
FIG. 17 is a front plan view of the package illustrated in FIG. 16 with portions cut away to show the articles contained therein.

One embodiment of a suitable package, indicated generally at 400, is illustrated in FIGS. 16 and 17. In the illustrated embodiment, the package 400 is adapted to receive a plurality of the male incontinence articles 10, 510 described above in a stacked configuration such that the cup 30 of the leading or overlying article is received in the cup of the trailing or underlying article (FIG. 17). In the specific embodiment illustrated in FIG. 17, the package 400 is adapted to receive two stacks of five stacked articles 10. The articles 10 being illustrated in FIG. 17 correspond to the article seen in FIGS. 1-6. Thus, the illustrated package 400 is adapted to receive ten total articles 10. It is understood, however, that the package 400 can be adapted to receive fewer stacks (i.e., one) of articles 10 or more stacks (i.e., 3 or more) without departing from some aspects of this disclosure. It is also understood that each of the stacks can have more or fewer than five articles 10 and that the package can be adapted to receive any suitable number of articles. It is further understood that the articles 10 can be placed in the package 400 in any suitable arrangements including non-stacked arrangements.

As seen in FIG. 16, the illustrated package 400 comprises a cylindrical tube 402 have a closed bottom 404 and a closure or lid 406. The lid 406 can be selectively removed by the user to gain access to the articles 10 positioned in the package 400, and replaced to reclose the package and thereby the articles remaining therein. The package 400 can be made from any suitable material including, but not limited to, cardboard, plastic, metal, or combinations thereof (e.g., the tube 402 can be made of cardboard and the bottom 404 and/or lid 406 can be made of plastic or metal). It is contemplated that the articles 10 can be packaged in other types of suitable packaging without departing from some aspects of this disclosure. For example, the bottom 404 of the package 400 can comprise a closure (similar to the lid 406 seen in FIG. 16) in addition to or instead of the top of the package. Thus, in one suitable embodiment, the package 400 can be opened from both the top and bottom of the package.

In the illustrated embodiment, at least the tube 402 of the package 400 is translucent thereby allowing the articles 10 contained therein to be at least partially visible through the tube. In a preferred embodiment, the articles 10 can be seen in the package 400 at any point about the circumference (i.e., 360 degrees) of the package 400. As a result, a user can readily see and identify the number of the articles 10 disposed within in the package 400. In one suitable embodiment, the package 400 includes indicia (e.g., text, symbols, pictures) correlating the 360 degree visibility of the articles 10 through the package 400 with the 360 degree protection provided to the male user by the articles. The articles 10 provide 360 degree protection to the wearer by fully capturing at least the distal end of the wearer's penis.

In another suitable embodiment, the entire package 400 (i.e., the tube 402, the bottom 404 and the lid 406) can be translucent. It is contemplated, however, that only a portion of the package 400 is translucent. For example, in one suitable embodiment, the package 400 includes a translucent band extending about the circumference of the package 400. It is also contemplated that all or parts of the package 400 can be transparent or opaque without departing from some aspects of this disclosure.

Figure 18:
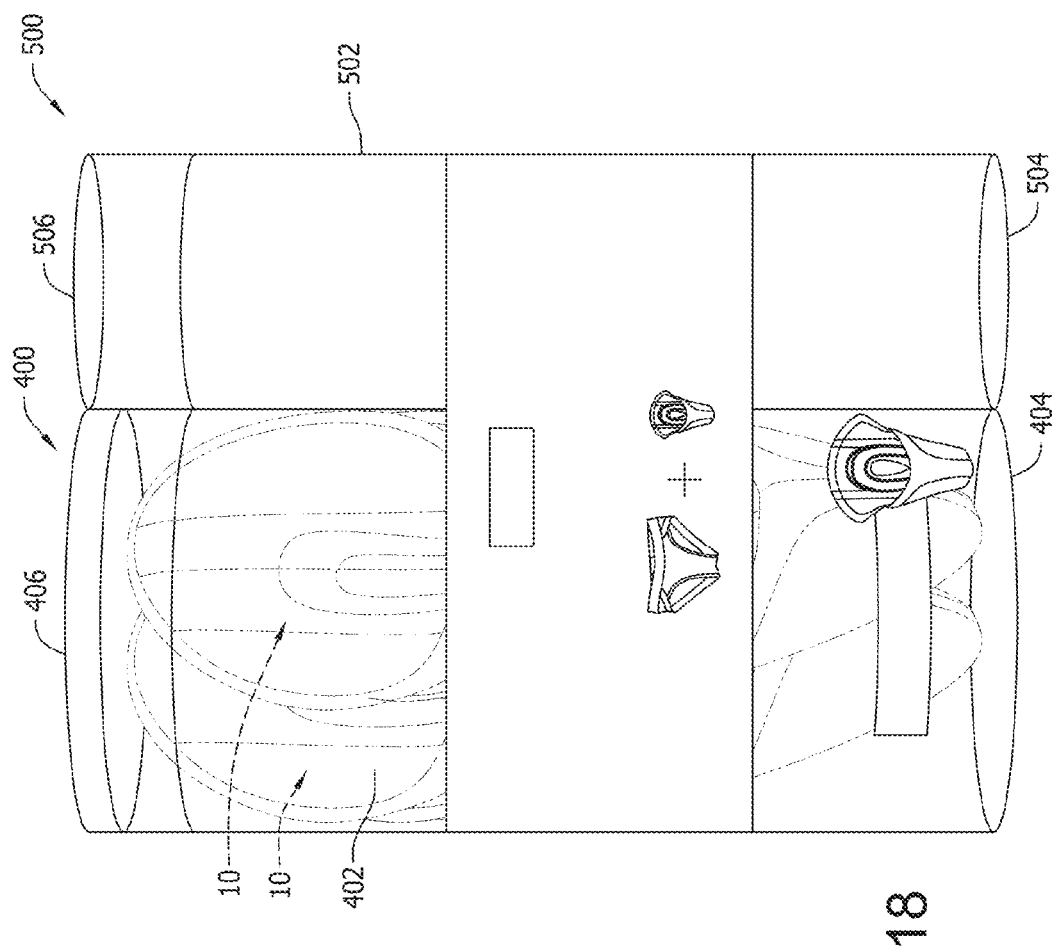
FIG. 18 is a front plan view of another suitable package containing a plurality of the male incontinence articles bundled with a package containing the underwear of FIG. 6.

FIG. 18 illustrates the package 400 bundled with another package, indicated generally at 500, containing at least one pair of the underwear 100 illustrated in FIGS. 8 and 9. The package 500 containing the underwear 100 is substantially the same as the package 400 but has a small diameter. Thus, the illustrated package 500 comprises a cylindrical tube 502 having a closed bottom 504 and a closure or lid 506. The lid 506 can be selectively removed by the user to gain access to the underwear 100 positioned in the package 500, and replaced to reclose the package and thereby the articles remaining therein. The package 500 can be made from any suitable material including, but not limited to, cardboard, plastic, metal, or combinations thereof (e.g., the tube 502 can be made of cardboard and the bottom 504 and/or lid 506 can be made of plastic or metal). It is contemplated that the articles 10 and the at least one underwear 100 can be packaged in the same package (e.g., package 400). It is further contemplated that the package 500 can include any number of underwear 100, for example, one, two, or three pairs of underwear may be provided in the package. It is also contemplated that the package 500 of underwear 100 does not need to be the same as or even similar to the package 400 of articles 10.

Figure 19:
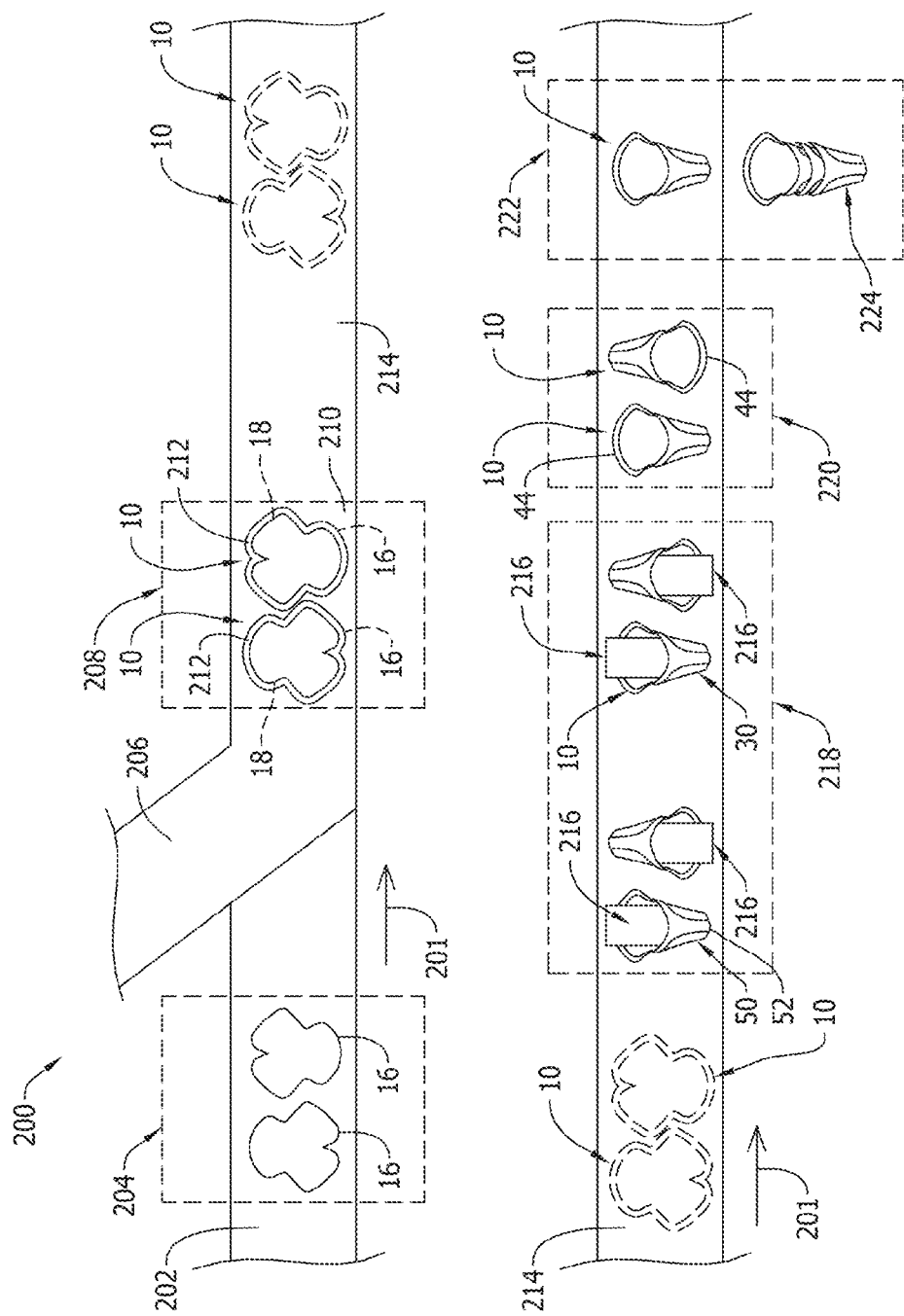
FIG. 19 schematically illustrates one suitable method and apparatus for manufacturing the male incontinence article shown in FIGS. 1-6.

FIG. 19 schematically illustrates one suitable method and apparatus, indicated generally at 200, for manufacturing the male incontinence article 10 shown in FIGS. 1-6. As illustrated in FIG. 19, a web 202 of suitable outer cover material (broadly, a first web) is fed in a machine direction, indicated by arrow 201 in FIG. 19, from a supply roll (not shown). Any suitable apparatus may be used to feed the web 202 of outer cover material in the machine direction 201 including, for example and without limitation, nip rolls, tensioning rolls, and combinations thereof. In the illustrated embodiment, the web 202 of outer cover material defines the outer cover 14 of the male incontinence article 10 (FIGS. 1-6), and is constructed of the same materials as the outer cover 14 described above with reference to FIGS. 1-6. It is contemplated, however, that in another suitable embodiment, the web 202 can be a suitable liner material and define the liner 12 of the male incontinence article 10.

Figure 20:
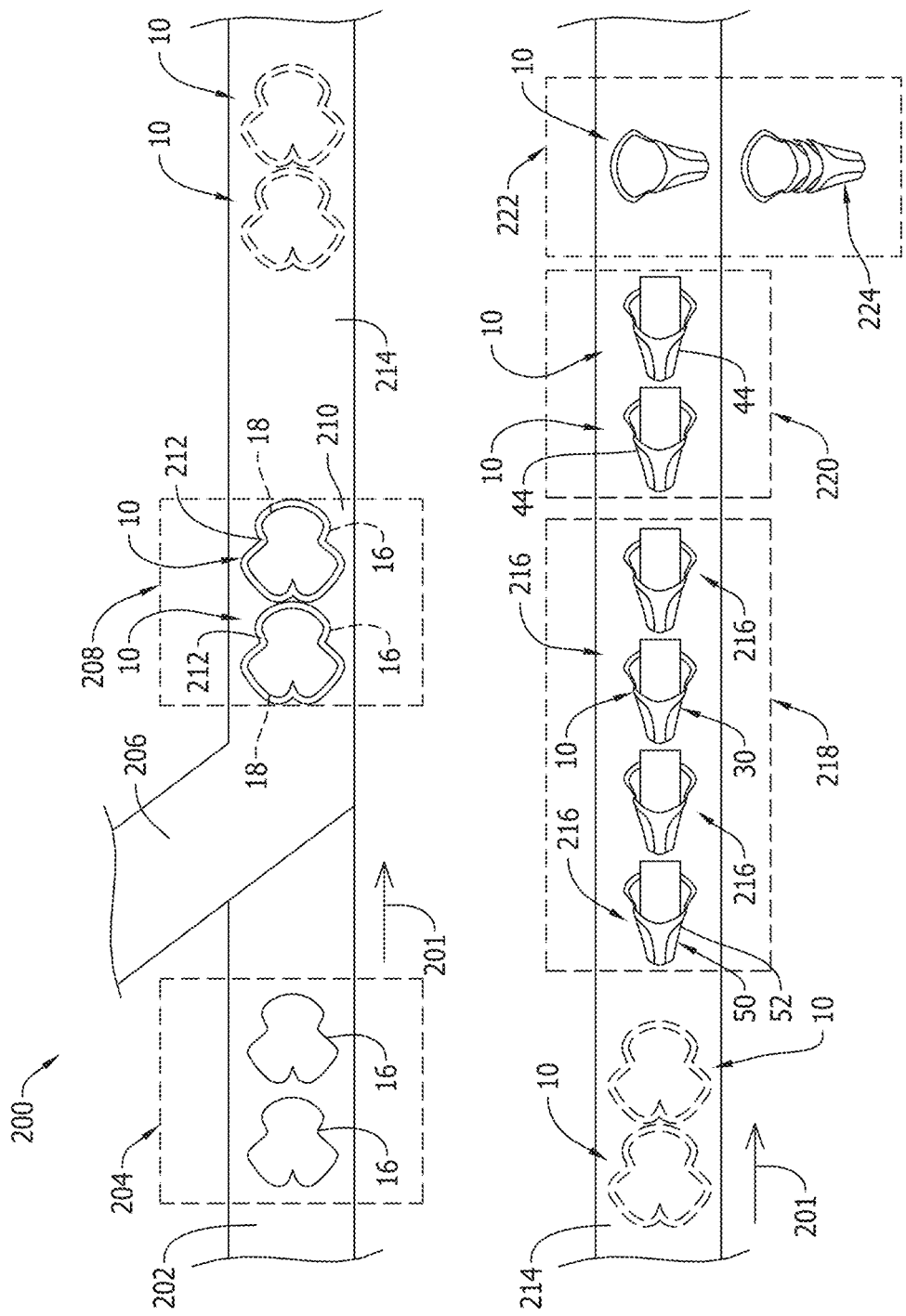
FIG. 20 schematically illustrates another suitable method and apparatus for manufacturing the male incontinence article shown in FIGS. 1-6.

Absorbent cores 16 are placed and attached to the web 202 of outer cover material at an absorbent core attachment station 204. In the illustrated embodiment, the absorbent cores 16 are placed on and attached to the web 202 of outer cover material in alternating orientations. That is, each absorbent core 16 is placed on and attached to the web 202 of outer cover material in an inverted (or opposite) orientation relative to the previously placed absorbent core 16. Further, the absorbent cores 16 are attached to the web 202 of outer cover material at a sufficient spacing from one another to permit a bond to be formed around each absorbent core 16, described in more detail below. In the illustrated embodiment, the absorbent cores 16 are placed on the web 202 in a cross machine direction orientation (i.e., the longitudinal axis of each of the absorbent core extends in the cross machine direction) but it is understood that the absorbent cores can be placed on the web in a machine direction orientation (i.e., the longitudinal axis of each of the absorbent core extends in the machine direction) as seen in FIG. 20.

Attaching the absorbent cores 16 to the web of outer cover material in alternating configurations facilitates nesting adjacent absorbent cores 16 with one another, and facilitates minimizing the amount of unused material per article 10 produced. It is understood that the absorbent cores 16 may instead be attached to the web 202 of outer cover material in substantially the same orientation. Further, although the absorbent cores 16 are shown as being attached to the web 202 of outer cover material in pairs, it is understood that the absorbent cores 16 may be attached to the web 202 of outer cover material in a substantially continuous manner. That is, the absorbent cores 16 may be attached to the web 202 of outer cover material at a continuous interval or spacing along the web 202 of outer cover material.

In some embodiments, the absorbent cores 16 are adhesively bonded to the web 202 of outer cover material. In such embodiments, adhesive is applied to the web 202 of outer cover material and/or the absorbent core 16 prior to the absorbent core 16 being attached to the web 202 of outer cover material. In other suitable embodiments, the absorbent cores 16 are attached to the web 202 of outer cover material using one of ultrasonic bonding, thermal bonding, pressure bonding, and combinations thereof. The absorbent core attachment station 204 may include any suitable apparatus to attach the absorbent core 16 to the web 202 of outer cover material including, for example and without limitation, adhesive applicators, compression rolls, nip rolls, laminator rolls, chill rolls, ultrasonic horns, anvils, and combinations thereof. It is contemplated that the absorbent cores 16 can be placed on the web 202 of outer cover material and not attached thereto.

A web 206 of liquid permeable liner material (broadly, a second web) is fed in the machine direction 201 from a supply roll (not shown), and is positioned in superposed relation with the web 202 of outer cover material. Any suitable apparatus may be used to feed the web 206 of liner material including, for example and without limitation, nip rolls, tensioning rolls, and combinations thereof. In the illustrated embodiment, the web 206 of liner material defines the liquid permeable liner 12 of the male incontinence article 10 (FIGS. 1-6), and is constructed of the same materials as the liquid permeable liner 12 described above with reference to FIGS. 1-6.

The web 206 of liner material is attached or bonded to the web 202 of outer cover material at a bonding and cutting station 208 to form a composite web 210. The web 206 of liner material is bonded to the web 202 of outer cover material at an attachment seam 212, which extends around the outer peripheral edge 18 of one of the absorbent cores 16 such that one of the absorbent cores 16 is interposed between the web 206 of liner material and the web 202 of outer cover material. The web 206 of liner material may be bonded to the web 202 of outer cover material by any suitable means including adhesives, ultrasonic bonds, thermal bonds, pressure bonds, and combinations thereof. Accordingly, the bonding and cutting station 208 may include any suitable apparatus to bond the web 206 of liner material to the web 202 of outer cover material including, for example and without limitation, adhesive applicators, compression rolls, nip rolls, laminator rolls, chill rolls, ultrasonic horns, anvils, and combinations thereof.

The composite web 210 is cut at the bonding and cutting station 208 to form the male incontinence article 10 in a laid flat configuration, as seen in FIGS. 1 and 2. With reference again to FIG. 19, the composite web 210 is cut around the outer peripheral edge 18 of each absorbent core 16 in a shape complementary to the outer peripheral edge 18 of the absorbent core 16. The bonding and cutting station 208 may include any suitable cutting apparatus to cut the composite web 210 including, for example and without limitation, rotary die cutters, oscillating water cutters, knife rolls, anvil rolls, and combinations thereof.

In the illustrated embodiment, the bonding and cutting operations are shown and described as being performed at a single station (i.e., the bonding and cutting station 208). In other suitable embodiments, the bonding and cutting operations may be carried out at separate stations, such as a dedicated bonding station and a dedicated cutting station. It is contemplated that the bonding and cutting operations can occur at various locations during the manufacture process. In one suitable embodiment, the cutting operation and thus the cutting station is located adjacent a packaging station, which is described in more detail below.

After the male incontinence articles 10 are severed from the composite web 210, the unused portions of the composite web 210 (i.e., portions of the web 202 of outer cover material and the web 206 of liner material) are directed away from subsequent processing stations of the method 200, and are discarded or recycled. Further, in the illustrated embodiment, a conveying member, such as a conveyor belt 214, directs the male incontinence articles 10 in the machine direction 201 to subsequent processing stations after the male incontinence articles 10 are severed from the composite web 210.

The lower portion 24 of each male incontinence article 10 (FIGS. 1 and 2) is formed or rolled about a forming member 216 at a forming station 218 to form the cup 30 of the male incontinence article 10 (FIGS. 4-6). More specifically, the side edges 31 of the lower portion 24 (FIGS. 1 and 2) are rolled about the forming member 216 into an overlapping relationship with one another (FIG. 15). The forming member 216 may include any suitable device configured to roll or form the lower portion 24 of the male incontinence article 10 about the forming member 216. The forming station 218 may include one or more suitable apparatus configured to cooperate with the forming member 216 to form the lower portion 24 of each male incontinence article 10 about the forming member 216. In one suitable embodiment, the forming member 216 comprises a cylindrical vacuum roll having a conically shaped tip configured to selectively apply a vacuum along desired portions of one of the male incontinence articles 10 (e.g., the lower portion 24) as the male incontinence article 10 passes between the forming member 216 and the conveying member 214.

After the lower portion 24 of the male incontinence article 10 is formed or rolled about the forming member 216, the overlapping portions of the lower portion 24 are bonded together to form the longitudinally extending seam 42 (FIG. 4) at the forming station 218. The overlapping portions of the lower portion 24 may be bonded together by any suitable means including adhesive bonds, ultrasonic bonds, thermal bonds, pressure bonds, sewing, hook and loop fasteners, and combinations thereof. The forming station 218 may include any suitable apparatus to bond the overlapping portions of the lower portion 24 together including, for example and without limitation, adhesive applicators, compression rolls, nip rolls, laminator rolls, chill rolls, ultrasonic horns, anvils, and combinations thereof. In the illustrated embodiment, the overlapping portions of the lower portion 24 are bonded together while the forming member 216 is disposed within the cup 30 of the male incontinence article 10. Thus, the forming member 216 may act as a bonding surface or nip roll to facilitate bonding the overlapping portions of the lower portion 24 together.

As seen in FIG. 19, when the lower portion 24 of the male incontinence article 10 is formed about the forming member 216, the lower portion 24 defines a conical portion 50 including a tip 52. The tip 52 of the conical portion 50 is tucked (or otherwise folded) and bonded to a portion of the outer cover 14 (FIG. 4) at the forming station 218 to seal the cup 30 of the male incontinence article 10, and form the closed bottom 32 of the cup 30 (FIGS. 4-6). The forming station 218 may include any suitable apparatus to tuck and bond the tip 52 of the conical portion 50 including, for example and without limitation, tucking fingers. In some embodiments, the tip 52 of the conical portion 50 may be inverted through the opening in the tip 52 before being tucked and bonded to the outer cover 14.

A covering material 44 is joined to the male incontinence article 10 along the longitudinally extending seam 42 (FIG. 4) at a cover application station 220 to cover the seam 42 and inhibit contact between the seam 42 and the user of the article 10. The covering material 44 may be joined to the male incontinence article 10 by any suitable means including, for example and without limitation, adhesive bonds, ultrasonic bonds, thermal bonds, pressure bonds, and combinations thereof. The cover application station 220 may include any suitable apparatus to bond the covering material 44 to the male incontinence article 10 including, for example and without limitation, adhesive applicators, compression rolls, nip rolls, laminator rolls, chill rolls, ultrasonic horns, anvils, and combinations thereof.

The male incontinence articles 10 are then oriented and packaged at an orientation and packaging station 222 using suitable orienting and packaging apparatus. In the illustrated embodiment, the male incontinence articles 10 are packaged in a stacked configuration. That is, the male incontinence articles 10 are packaged such that the cup 30 of each male incontinence article 10 is disposed within the cup 30 of another male incontinence article 10, with the exception of a leading male incontinence article, indicated at 224. In one suitable embodiment, the orientation and packaging station 222 is configured to orient and package the articles 10 as illustrated in FIGS. 17 and 18.

Figure 21:
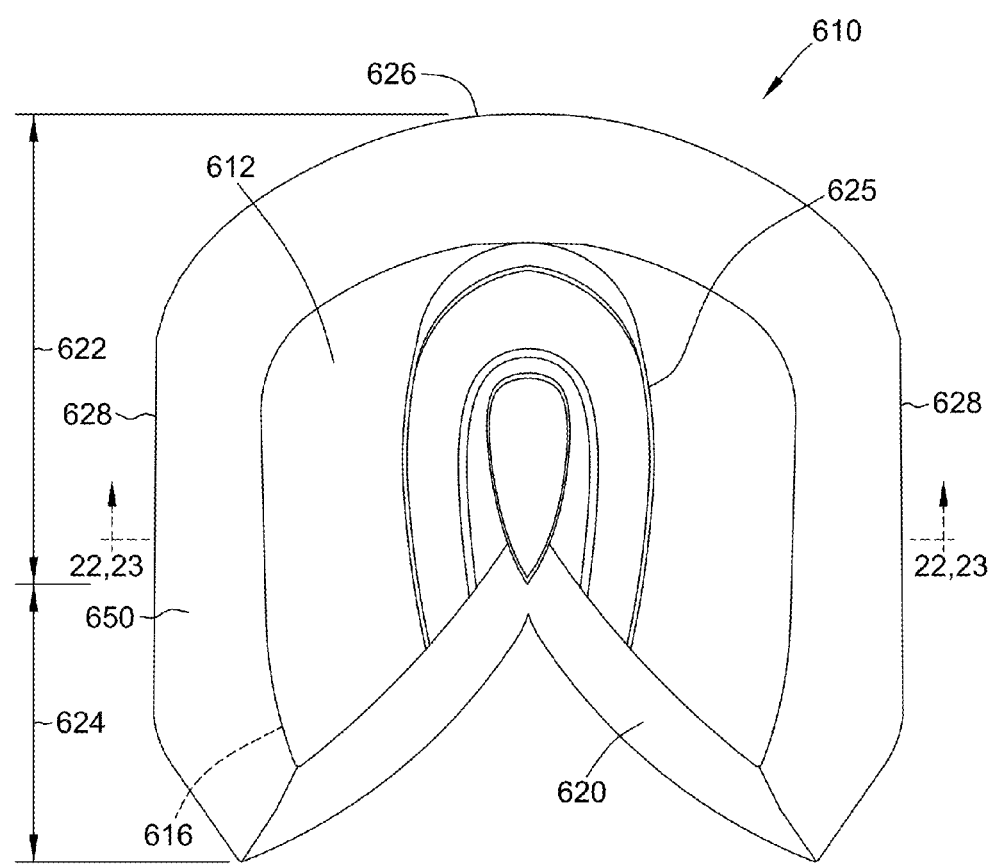
FIG. 21 is a front plan view of another suitable embodiment of a male incontinence article in a laid flat configuration showing a liquid permeable liner of the article.
Figure 22:
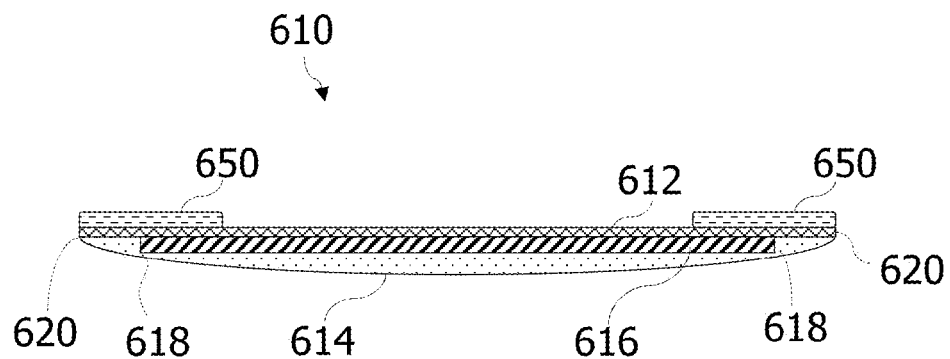
FIG. 22 is a cross sectional view of the male incontinence article of FIG. 21 in the laid flat configuration.
Figure 23:
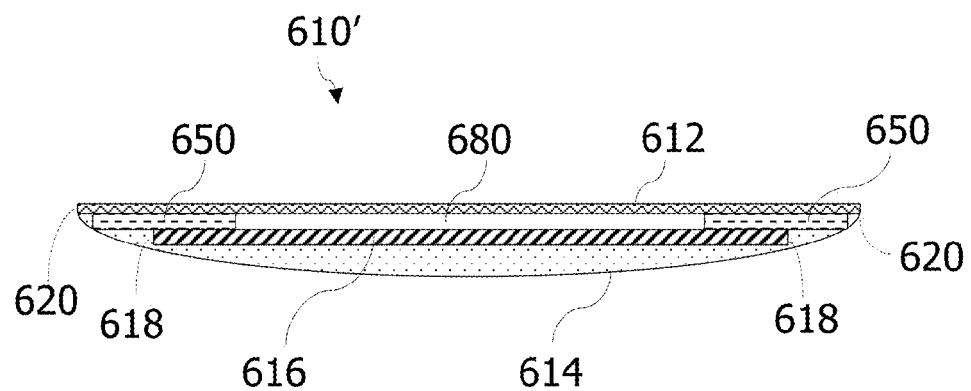
FIG. 23 is a cross sectional view of another suitable embodiment of a male incontinence article in a laid flat configuration similar to the male incontinence article shown in FIG. 21.
Figure 24A:
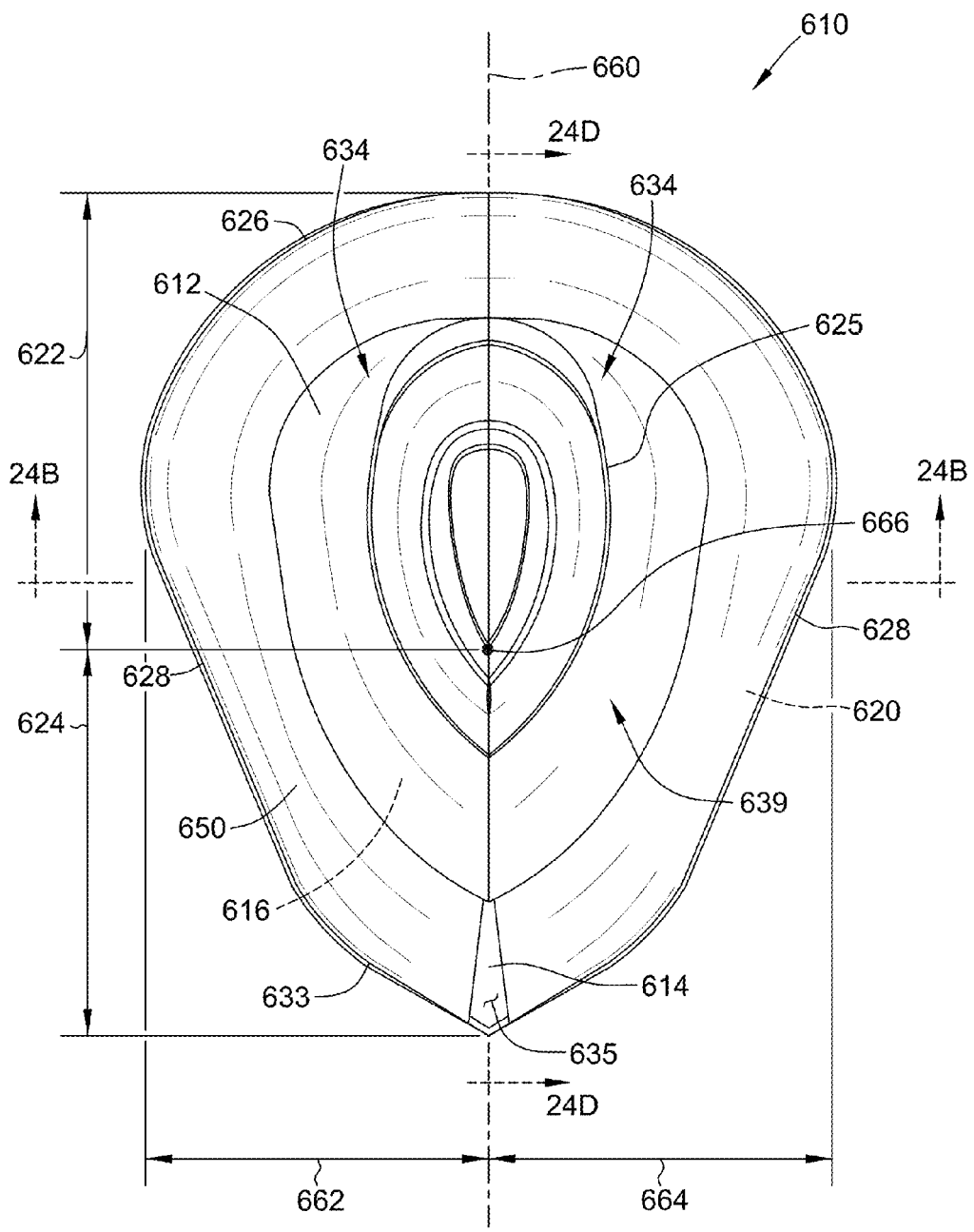
FIG. 24A is a front perspective view of the male incontinence article of FIG. 21 in a use configuration.
Figure 24B:
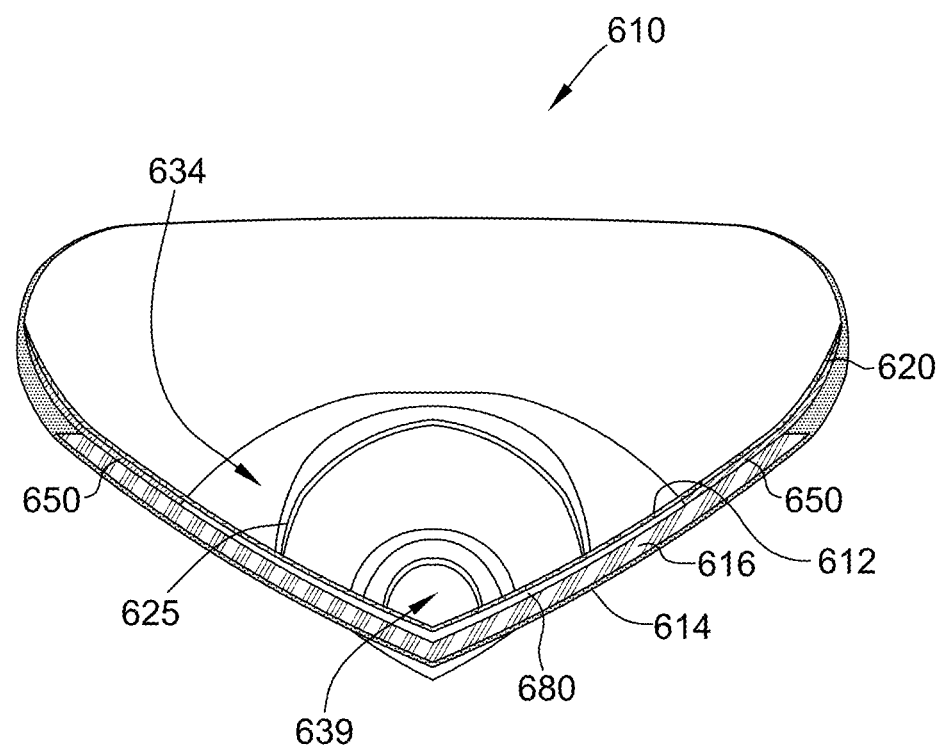
FIG. 24B is a cross sectional view of the article of FIG. 24A taken along line 24B-24B.
Figure 24C:
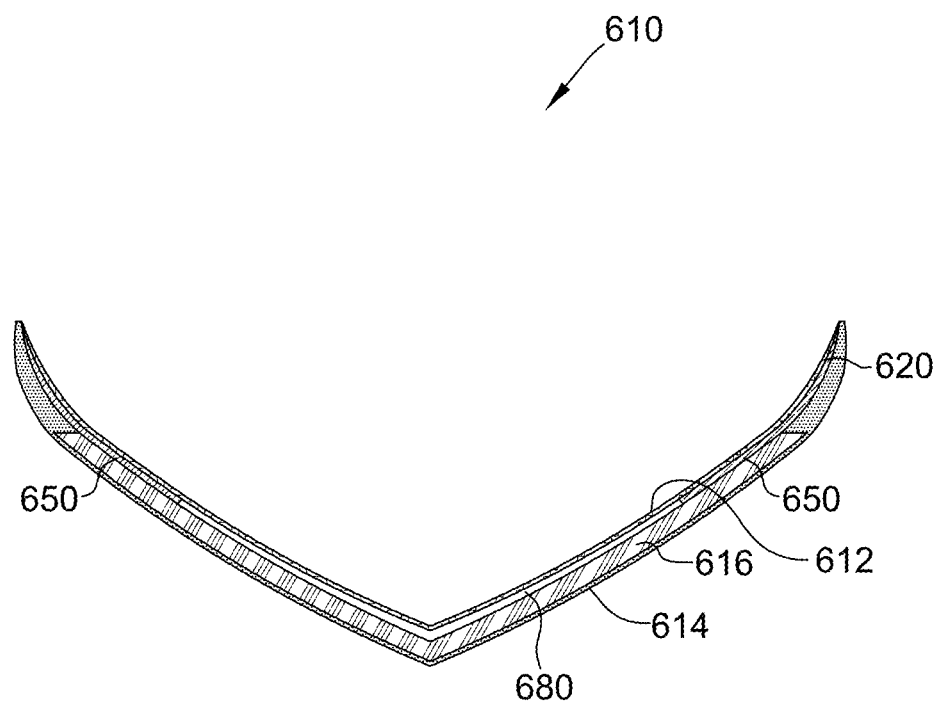
FIG. 24C is a cross sectional view similar to FIG. 24B but with portions of the article disposed behind the section line 24B-24B removed.
Figure 24D:
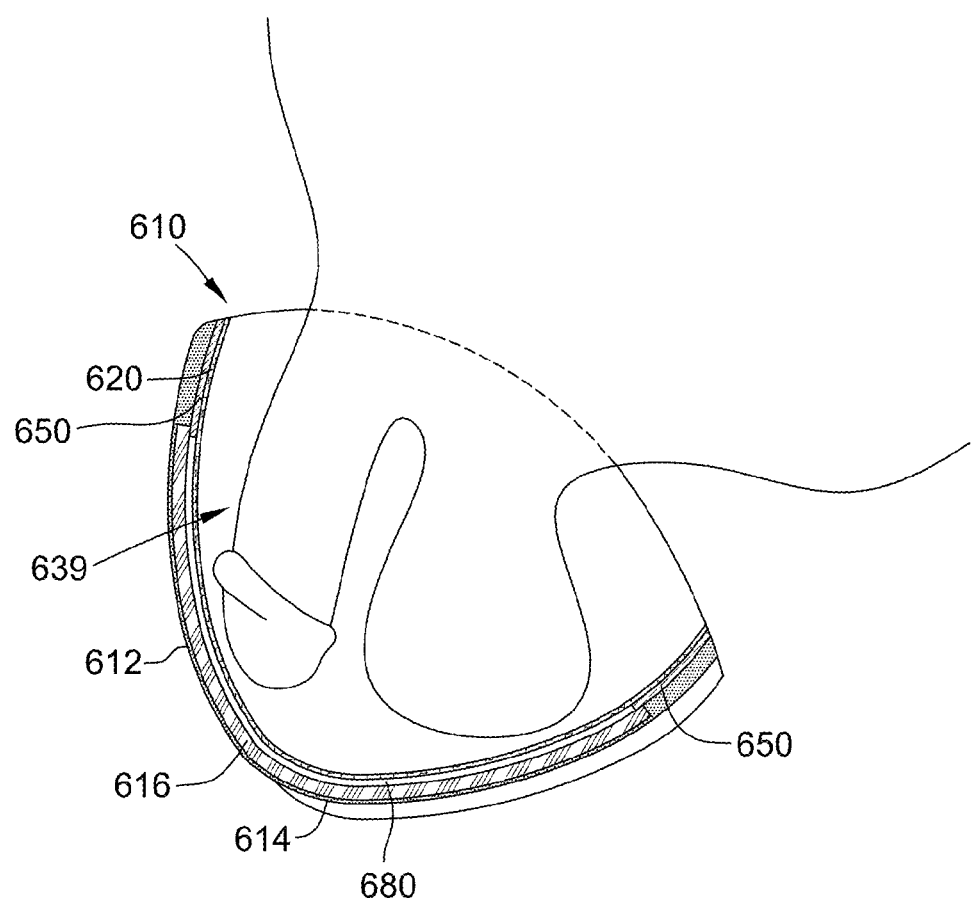
FIG. 24D is a cross sectional view of the article of FIG. 24A taken along line 24D-24D, the article being shown positioned relative to the male anatomy during use.
Figure 25:
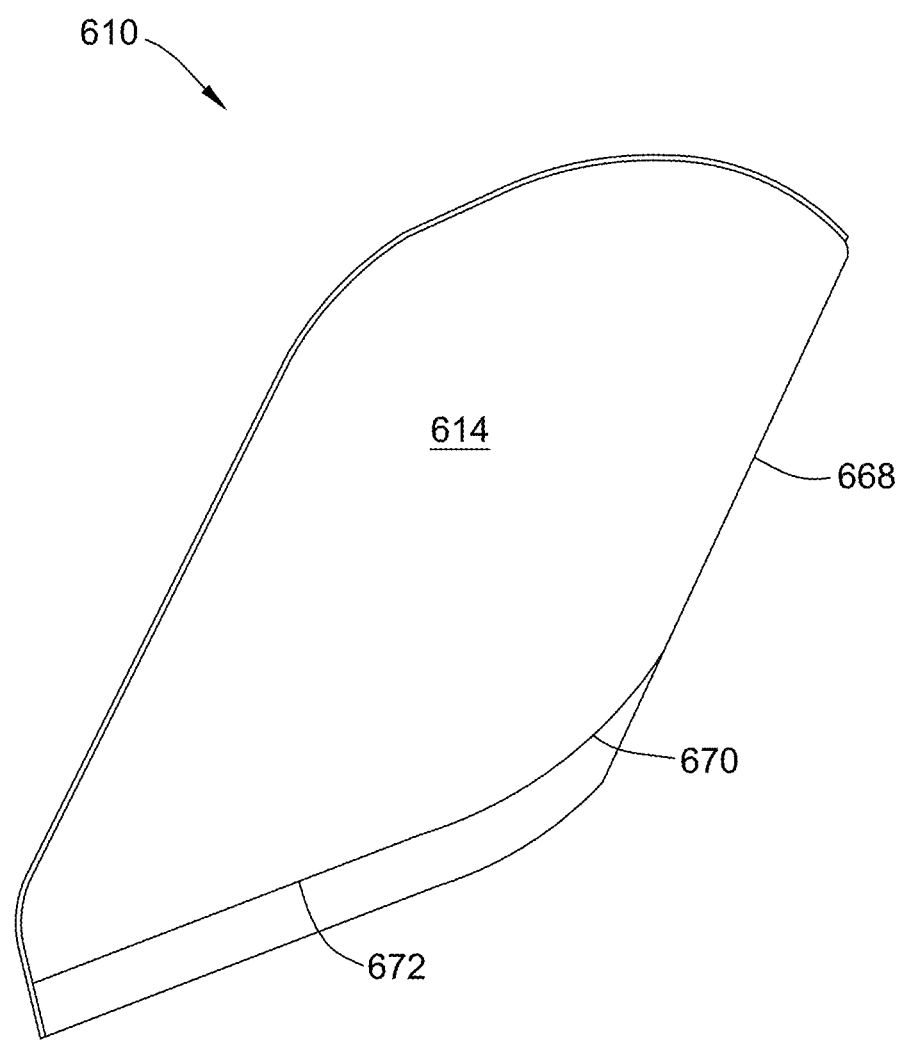
FIG. 25 is a side plan view of the male incontinence article of FIG. 22.

FIGS. 21-25 illustrate yet another suitable embodiment of a male incontinence article, indicated generally at 610, in accordance with this disclosure. The article 610 is substantially similar to the male incontinence article 10 shown in FIGS. 1-6 except the article 610 does not include any lobes to form a pocket. Rather, in the illustrated embodiment, the article 610 includes a bumper or gasket-like structure to facilitate retention of fluids. FIG. 21 illustrates the male incontinence article 610 in a laid flat configuration. FIGS. 22 and 23 depict a cross sectional view of the male incontinence article 610 and a similar embodiment of a male incontinence article indicated generally as 610' at line 22,23-22,23 shown in FIG. 21. In the absence of contrary representation, the article 610' is substantially the same as the article 610 and therefore will not be described in detail. FIGS. 24A and 25 illustrate the article in a use configuration.

In one suitable embodiment, the article 610 is provided to the user in the use configuration. That is, the article 610 is provided (e.g., by the manufacturer) in the use configuration illustrated in FIGS. 24 and 25 such that the article is ready-for-use by the male user upon removal of the article from a suitable package and without requiring any manipulation of the article by the user prior to use. In another suitable embodiment, the article 610 is provided to the user in the laid flat configuration illustrated in FIG. 21. In such an embodiment, the article 610 is adapted to be manually manipulated by the user to reconfigure the article from the laid flat configuration illustrated in FIG. 21 to the use configuration illustrated in FIG. 24A. In other suitable embodiments, the article 610 is provided to the user in a collapsed configuration. That is, the article is provided such that the user opens or otherwise manipulates the article 610 into the use configuration prior to use.

In one suitable embodiment, a plurality of the articles 610 can be packaged as described above with respect to FIGS. 16-18. In other suitable embodiments, a plurality of the articles 610 can be packaged stacked in the laid flat configuration or the collapsed configuration. It is contemplated that the articles 610 can be individually wrapped using any suitable wrapper. The wrapped articles 610 can be in the laid flat configuration, the collapsed configuration, or the use configuration. In addition, the wrapped articles 610 can be provided to the user individually or packaged as a plurality of the articles.

As explained in more detail below, the male incontinence article 610 in its use configuration (FIG. 24A) is suitably sized and shaped for receiving at least a portion of user's penis (i.e., at least the distal end of the user's penis having the urethra opening) and is adapted to take-in and retain fluids (e.g., urine, semen, sweat) discharged from the user's penis. The article 610 illustrated in FIGS. 21 and 24A is particularly adapted to take-in and retain urine associated with incontinence. In one suitable embodiment, the male incontinence article 610 in its use configuration is suitably sized for receiving both the user's penis and scrotum. For example, FIG. 24D is a cross-sectional view illustrating the article 610 position relative to the user's penis and scrotum. As seen therein, the male incontinence article 610 is suitably sized for receiving both the user's penis and scrotum.

The male incontinence article 610 seen in FIGS. 21, 22, and 24A comprises a liquid permeable liner 612, a liquid impermeable outer cover 614, and an absorbent core 616 disposed between the liner and the outer cover. The liner 612, the outer cover 614, and the absorbent core 616 are substantially the same as the liner 12, the outer cover 14, and the absorbent core 16 described above with respect to FIGS. 1-6. As a result, the liner 612, the outer cover 614, and the absorbent core 616 will not be described again in detail.

The liner 612 and the outer cover 614 of the illustrated embodiment are secured (i.e., bonded) together along their respective peripheral edges and outboard of the absorbent core 616 (see, e.g., FIGS. 22 and 23). More specifically, both the liner 612 and the outer cover 614 extend beyond an outer peripheral edge 618 (shown in FIGS. 22 and 23) of the absorbent core 616 and are bonded together to form a peripheral seal using any suitable bonding technique (e.g., adhesives, ultrasonic bonds, thermal bonds, pressure bonds, or combinations thereof) to define a bonded area 620 (FIG. 21). In one suitable embodiment, the absorbent core 616 can be bonded to the liner 612 and/or the outer cover 614. In another suitable embodiment, the absorbent core 616 is not bonded to either the liner 612 or the outer cover 614. Rather, the absorbent core 616 is captured between the liner 512 and the outer cover 614 as shown, for example, in FIGS. 22 and 23.

As illustrated in FIGS. 21, 22, and 24A, the article 610 includes a barrier 650 that extends adjacent the perimeter of the liner 612. In some suitable embodiments, the barrier 650 is formed separately from and bonded to one of the liner 612 or the outer cover 614 at the bonded area 620. In the illustrated embodiment, the barrier 650 is bonded to the liner 612. As a result, the barrier 650 and the bonded area 620 are at least in part coextensive. In one suitable embodiment (FIG. 22), the barrier 650 at least in part overlies the bonded area 620. In other suitable embodiments the barrier 650 can be disposed, at least in part (FIG. 22) or in whole (FIG. 23), inboard of the bonded area 620. In other embodiments, the liner 612 and the outer cover 614 may extend beyond the barrier 650 and are bonded together to form a peripheral seal using any suitable bonding technique to secure the barrier 650. It is contemplated that the barrier 650 can be formed integrally with either the liner 612 or the outer cover 614. In other words, the barrier 650 can be formed as a single piece with either the liner 612 or the outer cover 614. For example, the barrier 650 and the liner 612 can be formed as a single piece via an airlaid process.

Suitably, the barrier 650 is configured to inhibit leakage and provide a comfortable fit to the user. The selection of such barrier material can vary based upon the overall attributes of the barrier 650. For example, the barrier 650 can be made of a hydrophilic material to absorb leakage. In another embodiment, the barrier 650 can be made of a hydrophobic material to inhibit liquid from leaking past the article 610. In some embodiments, the barrier 650 may be a two layer or multi-component material such as, for example, a hydrophobic material adjacent to a user's skin (i.e., to prevent discomfort from body fluids against the user's skin) and a hydrophilic material adjacent to the liner 612. In some embodiments, the barrier 650 is made of materials that reduce the discomfort of the user while using the article 610.

For example, the barrier 650 may be made of soft, non-abrasive, and/or elastic materials. In one suitable embodiment, the barrier 650 provides a gasket against the wearer's skin during use of the article 610 to inhibit leakage of liquid (e.g., urine).

In suitable embodiments, the barrier 650 can be made of thru air bonded carded web (TABCW, also known as surge), foam, airlaid, coform, fluff, SAM/fluff, apertured film (alone or laminated to a suitable nonwoven), nonwoven/film laminates (which can be elastic or non-elastic), meltblown, hydroentangled nonwovens for added loft/bulk, and any suitable combination thereof. These suitable materials can be used alone or in combination with suitable embossing or bonding techniques.

With respect now to FIGS. 22 and 23, the barrier 650 creates space between the user the article 610, 610'. Creating space may inhibit the user from contacting the wet absorbent core and/or providing more room to accommodate the user's penis in the article 610, 610'. The additional bulk or loft of the barrier 650 prevents gaps between the user and the barrier 650 that may cause leakage during use. The barrier 650 is configured to prevent gaps even while the user is performing a physical activity (e.g., walking, running, etc.). It is to be understood that the articles 610, 610' may include different configurations than what is illustrated in FIGS. 22 and 23.

In FIG. 22, the barrier 650 is attached to the article 610 at the bonded area 620. In FIG. 23, the liner 612 and the outer cover 614 are bonded at the bonded area 620 to enclose the barrier 650. Due to the additional bulk or height of the barrier 650, a gap 680 may be defined between the liner 612 and the absorbent core 616. In certain embodiments, another layer may be coupled to the absorbent core 616. The gap 680 enables the liner 612 to conform to the user and prevent leakage. In the illustrated embodiment, the entire liner 612 is spaced from the absorbent core 616. In other suitable embodiments, a portion of the liner 612 (e.g., a central portion of the liner) can be configured such that it is adjacent to or in contact with the absorbent core 616.

As illustrated in FIG. 21, the male incontinence article 610 in the laid flat configuration has an upper portion 622 and a lower portion 624. The upper portion 622 includes an arcuate upper edge 626 and a pair of side edges 628 that extend downward to the lower portion 624. The lower portion 624 includes a generally W-shaped lower edge 633 extending between the pair of side edges 628. The article 610 in its laid flat configuration, as seen in FIG. 21, can be sized similar to the article 10 of FIG. 1 in its laid flat configuration. More specifically, the article 610 in the laid flat configuration can have a greatest length, which is defined as the longitudinal distance between longitudinally outermost extents of the article, in the range of about 100 mm to about 350 mm, and more suitably in the range of about 120 mm to about 250 mm. In the illustrated embodiment, for example, the absorbent article 610 has a greatest length of about 180 mm. A greatest width of the article 610, which is defined as the lateral distance between lateral outermost extents of the article, is in the range of about 120 mm to about 350 mm and more suitably about 120 mm to about 250 mm. In the illustrated embodiment, for example, the greatest width of the article 610 is approximately 180-200 mm. It is understood that the absorbent article 610 can have any suitable greatest length and any suitable greatest width including lengths and widths different than those set forth above without departing from some aspects of this disclosure.

In the illustrated embodiment shown in FIG. 21, the lower portion 624 has a generally V-shaped cutout 635 that extends upward through the lower edge 633 and a portion of the liner 612. The cutout 635 enables the male incontinence article 610 to provide flexibility and various fits to users. In certain embodiments, the outer cover 614 does not include the cutout 635 and is continuous along the lower edge 633 to block body fluids from leaking past the article 610 via the cutout 635. It is understood that, in other suitable embodiments, the cutout 635 can have any suitable shape including, but not limited to, U-shaped, or semicircular. It is also understood that in some suitable embodiments, the cutout 635 can be omitted. In such an embodiment, the lower edge 633 of the lower portion 624 would be continuous instead of bifurcated as seen, e.g., in FIG. 21.

It is contemplated that other suitable shapes and/or sizes for the article 610 in its laid flat configuration can be used, provided that the shape and size of the article will allow it to be configured to its use configuration (FIG. 22).

In one suitable embodiment and as seen in FIG. 21, an aesthetic feature or visual cue 625 is visible through or is disposed on the liner 612 to assist the user in either properly aligning the article 610 during use or highlighting regions. The visual cue 625 is substantially the same as the visual cue 25 described above with respect to FIGS. 1-6. It is contemplated that other suitable visual cues can be provided on the article 610.

As seen in FIG. 24A, the article 610 further includes a folding line 660 along the longitudinal axis of the article that defines a first side portion 662 and a second side portion 664. In one suitable embodiment, the folding line 660 extends the entire longitudinal length of the article 610. In another suitable embodiment, the folding line 660 partially extends the longitudinal length of the article 610 (e.g., the folding line 660 may not extend through the bonded area 620). The folding line 660 enables the article 610 to be manipulated from the laid flat configuration (FIG. 21) or the collapsed configuration (e.g., where the right side of the article or second side portion 664 as illustrated in FIG. 24A is folded over the left side of the article or first side portion about the folding line 660 such that the first and second sides of the article are in face-to-face relationship) to the use configuration (FIG. 24A).

With reference now to FIG. 24A, the male incontinence article 610 is illustrated in its use configuration. Thus, either the user was provided the article 610 in the use configuration upon removal of the article from a suitable package or the user manually manipulated the article from the laid flat configuration illustrated in FIG. 21 or the collapsed configuration to the use configuration illustrated in FIG. 24A. FIG. 24A is a front perspective of the male incontinence article 610 illustrating the body-facing side of the article. That is, during use of the article 610, the side of the article seen in FIG. 24A is adapted to face and to be in at least partial engagement with the skin of the user. The opposite side of the article 610 is the garment facing side or the portion of the article that faces away from the user during use. FIGS. 24B and 24D are transverse and longitudinal cross-sections, respectively, of the article 610 seen in FIG. 24A.

As seen in FIGS. 24A, 24B and 24D, the article, in its use configuration, is generally ovate and defines a chamber or pocket, indicated generally at 639, that is sized and shaped to receive at least the distal end of the user's penis having the urethra opening. In the illustrated embodiment, the liner 612, the outer cover 614 and the absorbent core 616 are ovate and cooperatively define the pocket 639. The first and second side portions 662, 664 of the article are drawn towards each other to define a pair of opposing sidewalls 634 of the chamber 639 centered on the folding line 660. Opposite portions of the liner 612 and/or the bonding area 620 across the folding line 660 may be secured together to maintain the article 610 in the use configuration or the collapsed configuration. For example, the liner 612 and/or the bonding area 620 may be secured by fasteners, adhesive, tape, hook and loop, buttons, and/or snaps. In another suitable embodiment, the outer cover 614 is continuous across the cutout 635 and secures the article in the use configuration or the collapsed configuration.

In one suitable embodiment, the pocket (or chamber) 639 has a volume between 100 ml and 1,000 ml. More suitably, the pocket has a volume between 200 ml and 600 ml and, even more suitably, between 250 ml and 500 ml. The volume of the pocket 639 defines the amount of three-dimensional space enclosed within the article 610. In other words, the volume defines the amount of space defined by the article 610 that is adapted to receive the user's penis and/or scrotum.

In the illustrated embodiment, the sidewalls 634 are coupled together at an angle to attract body fluids to a recessed location indicated generally at 666 to reduce the risk of leakage. In other suitable embodiments, the recessed location 666 may be at a different location within the chamber 639. By directing unabsorbed body fluids to the recessed location 666, the article 610 may reduce the amount of body fluids near the perimeter of the article 610 and prevent leakage. In certain embodiments, the recessed location 666 includes additional absorbent material for retaining the body fluids.

FIG. 25 is a side plan view of the article 610 in the use configuration. The article 610 has a first outer edge 668, a transition edge 670, and a second outer edge 672. In other suitable embodiments, the article 610 may include more or less outer edges. In the illustrated embodiment, the transition edge 670 is coupled between the first outer edge 668 and the second outer edge 672. The first outer edge 668 is coupled to the transition edge 670 at an angle different than the second outer edge 672 to form the chamber 639. In some embodiments, the first outer edge 668, the transition edge 670, and the second outer edge 672 form a generally arcuate shape. In the illustrated embodiment, the first outer edge 668 and the second outer edge 672 are generally straight lines.

In certain embodiments, the article 610 may include any suitable fasteners (e.g., adhesive, tape, hook and loop, buttons, snaps) to hold the article in position. The first outer edge 668 of the article 610 is situated such that body fluids that contact the upper portion 622 of the article 610 generally are directed to the recessed location 666 shown in FIG. 22. Body fluids that contact the lower portion 624 may be directed to the lower edge 633 of the article 610 rather than the recessed location 666. In at least one suitable embodiment, the lower portion 624 is positioned at a slight decline to slow down unabsorbed body fluids from leaving the article 610.

The barrier 650 is at least partially in contact with the user's skin or garments. In certain embodiments, the barrier 650 provides at least a partial fluid seal or gasket between the user's skin or garments and the male incontinence article 610. When the user moves throughout the day, the barrier 650 may adapt to the user's movement (i.e., maintain contact with the user's skin or garments) to prevent leakage while enabling the user to move freely with little discomfort. It is to be understood that the male incontinence article 610 may be aligned in a different position due to the user's preference and/or other considerations such as a different configuration of the article 610.

Figure 26:
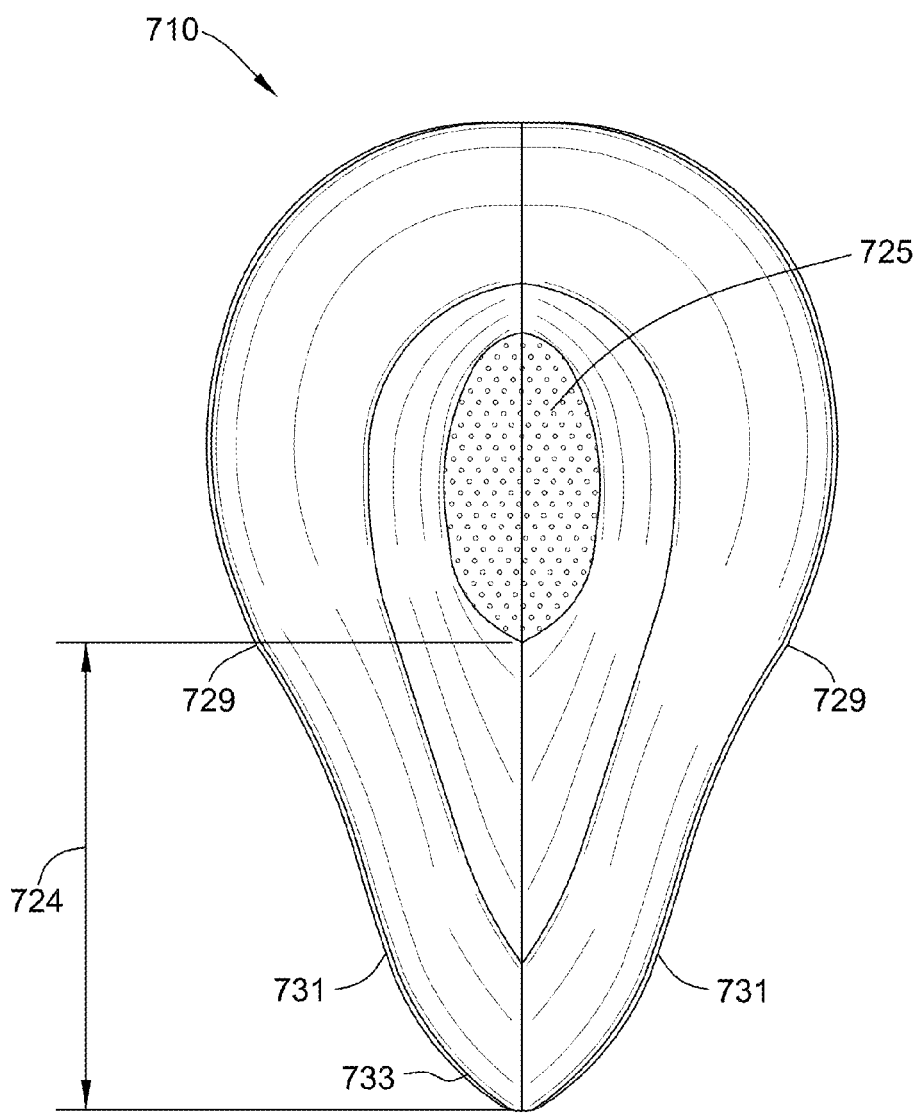
FIG. 26 is a front plan view of another suitable embodiment of a male incontinence article in a use configuration showing a liquid permeable liner of the article.

FIG. 26 illustrates another suitable embodiment of a male incontinence article, indicated generally at 710, in accordance with this disclosure. The article 710 seen in FIG. 26 is substantially the same as the article 610 seen in FIGS. 21-25 except that the article 710 includes a lower portion 724 and a visual cue 725. The lower portion 724 includes a pair of side edges 731, a generally arcuate lower edge 733, and a cutout 735. The side edges 731 taper outwardly from the transition 729 to the lower edge 733. The lower edge 733 is a generally arcuate shape coupled between the side edges 731. The visual cue 725 is a circular design with dots for aligning the user's penis with the article 710.

Figure 27:
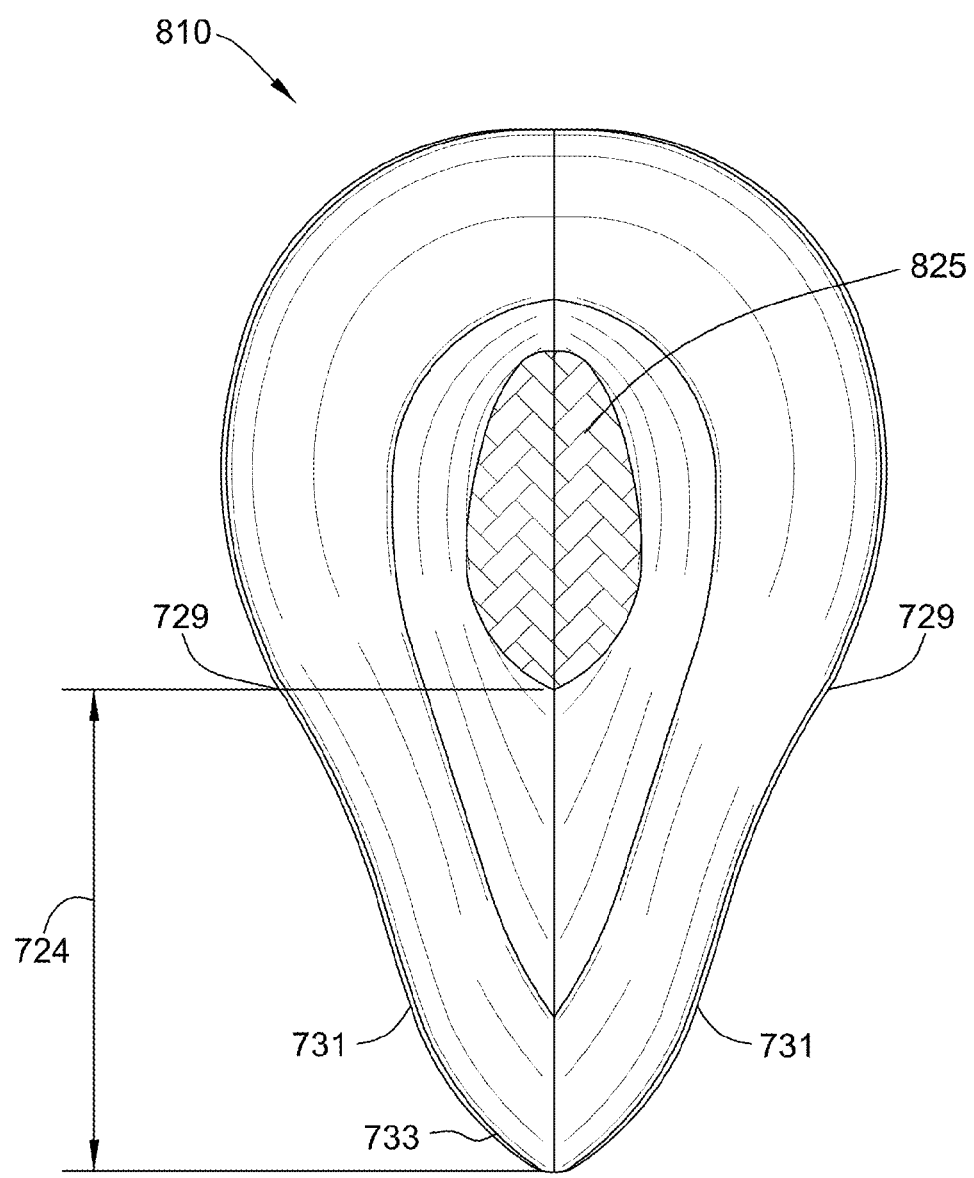
FIG. 27 is a front plan view of another suitable embodiment of a male incontinence article in a use configuration showing a liquid permeable liner of the article.

FIG. 27 illustrates another suitable embodiment of a male incontinence article, indicated generally at 810, in accordance with this disclosure. The article 810 seen in FIG. 27 is substantially the same as the article 610 seen in FIGS. 21, 22, and 24 except that article 810 includes the lower portion 724 shown in FIG. 26 with article 710 and a visual cue 825. In at least one suitable embodiment, the visual cue 825 is an absorbent pad with a woven material design. The absorbent pad provides additional support for absorbing body fluids at certain locations within the article 810 such as, for example, directly in front of the user's penis when the user's penis is aligned. The visual cue 825 may be made of materials similar to the liner 612 and the absorbent core 616 (both shown in FIGS. 21 and 22). In certain embodiments, the liner 612 is coupled between the absorbent core 616 and the visual cue 825. In other embodiments, the absorbent core 616 may be coupled to or replace the visual cue 825.

With respect to the articles shown in FIGS. 21-27, the articles may be packaged similarly to embodiments shown in FIGS. 16-18. The articles may be made using a similar process to the process shown in FIGS. 19 and 20.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products without departing from the scope of the invention, it is intended that all matter contained in the above description and shown in the accompanying drawings shall be interpreted as illustrative and not in a limiting sense.

What is claimed is:

1. A male incontinence article comprising:
   a liquid permeable liner positioned to contact a male user's penis when the article is worn by the male user, the liner having a peripheral edge;
   a liquid impermeable outer cover having a peripheral edge;
   an absorbent core disposed between the liner and the outer cover, the absorbent core having a peripheral edge; and
   a barrier positioned adjacent the peripheral edges of the liner and the outer cover, wherein the barrier is coextensive with the peripheral edges when the article is in a use configuration, the barrier including an outer surface and an inner surface, the outer surface being configured to engage the male user's skin and form a seal, wherein the barrier lies on the liner such that the entire inner surface of the barrier is in contact with the liner.

2. The male incontinence article set forth in claim 1 wherein the peripheral edges of the liner and the outer cover extend beyond the peripheral edge of the absorbent core, the liner and the outer cover being secured together along their respective peripheral edges to define a bonded area disposed outboard of the peripheral edge of the absorbent core.

3. The male incontinence article set forth in claim 2 wherein the barrier is bonded to the liner at the bonded area.

4. The male incontinence article set forth in claim 3 wherein the barrier at least in part overlies the bonded area.

5. The male incontinence article set forth in claim 2 wherein the barrier is disposed, at least in part, inboard of the bonded area.

6. The male incontinence article set forth in claim 1 wherein the barrier is configured to create a space between the article and the male user.

7. The male incontinence article set forth in claim 1 wherein the barrier overlies the liner.

8. A male incontinence article comprising:
a liquid permeable liner having a peripheral edge;
a liquid impermeable outer cover having a peripheral edge,
an absorbent core disposed between the liner and the outer cover, the absorbent core having a peripheral edge, the peripheral edges of the liner and the outer cover extending beyond the peripheral edge of the absorbent core, the liner and the outer cover being secured together along their respective peripheral edges and outboard of the peripheral edge of the absorbent core;
wherein the liner, outer cover, and absorbent core in their entire cooperative capacity are ovate and cooperatively define a pocket that is sized and shaped to receive at least a distal end of a male user's penis; and
a barrier coextensive with the peripheral edges of the liner and the outer cover when the article is in a use configuration.

9. The male incontinence article set forth in claim 8 wherein the absorbent core is bonded to at least one of the liner and the outer cover.

10. The male incontinence article set forth in claim 8 further comprising a visual cue configured to assist the male user during use in aligning at least the distal end of the male user's penis with the visual cue.

11. The male incontinence article set forth in claim 8 wherein the article is provided to the male user in a laid flat configuration.

12. The male incontinence article set forth in claim 8 wherein the article is provided to the male user in a collapsed configuration wherein a first portion of the article is folded over a second portion of the article about a longitudinally extending folding line such that the first portion and second portion are in face-to-face relationship.

13. The male incontinence article set forth in claim 8 wherein the article is provided to the male user in a use configuration.

14. A package comprising a plurality of the male incontinence articles set forth in claim 8 in a stacked configuration wherein overlying articles are nested with the respective underlying article, the package comprising a cylindrical tube having a bottom and a lid, at least one of the bottom and the lid being selectively removeable to provide access to the articles positioned in the tube.

15. The package set forth in claim 14 wherein the tube is translucent or transparent about its entire circumference.

16. A male incontinence article comprising:
a liquid permeable liner having a peripheral edge;
a liquid impermeable outer cover having a peripheral edge;
an absorbent core disposed between the liner and the outer cover, the absorbent core having a peripheral edge and the peripheral edges of the liner and the outer cover extending beyond the peripheral edge of the absorbent core, the liner and the outer cover being secured together along their respective peripheral edges to define a bonded area disposed outboard of the peripheral edge of the absorbent core; and
a barrier extending adjacent the perimeter of the liner, the barrier being bonded to the liner at the bonded area,
wherein the article further comprises an upper edge, a lower edge, side edges extending between the upper edge and the lower edge, and the barrier is disposed along a majority of the upper edge, a majority of the lower edge, and a majority of the side edges when in a use configuration.

17. The male incontinence article set forth in claim 16 wherein the barrier overlies the liner.

18. The male incontinence article set forth in claim 16 wherein the barrier underlies the liner.

19. The male incontinence article set forth in claim 1, wherein the liner, outer cover, and absorbent core are ovate and cooperatively define a pocket that is sized and shaped to receive at least a distal end of the male user's penis.

20. The male incontinence article set forth in claim 19, wherein the pocket tapers outward from a first width at a bottom of the pocket to a second width at a top of the pocket, the second width is greater than the first width.

21. The male incontinence article set forth in claim 1, wherein the liner, the outer cover, the absorbent core, and the barrier define a thickness of the male incontinence article, and wherein the thickness is less than 6 millimeters.

22. The male incontinence article set forth in claim 3 wherein the barrier and the bonded area are coextensive.

* * * * *